US009427333B2

(12) United States Patent
Satterthwaite

(10) Patent No.: US 9,427,333 B2
(45) Date of Patent: Aug. 30, 2016

(54) SURGICAL INSTRUMENT AND METHOD OF POSITIONING AN ACETABULAR PROSTHETIC COMPONENT

(71) Applicant: DEPUY SYNTHES PRODUCTS, INC., Raynham, MA (US)

(72) Inventor: Rodney E. Satterthwaite, Huntington, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 14/710,042

(22) Filed: May 12, 2015

(65) Prior Publication Data
US 2015/0238326 A1    Aug. 27, 2015

Related U.S. Application Data

(62) Division of application No. 13/786,845, filed on Mar. 6, 2013, now Pat. No. 9,055,975.

(60) Provisional application No. 61/707,904, filed on Sep. 29, 2012.

(51) Int. Cl.
*A61F 2/46* (2006.01)
*A61B 17/58* (2006.01)
(Continued)

(52) U.S. Cl.
CPC ............. *A61F 2/4609* (2013.01); *A61B 17/58* (2013.01); *A61F 2/34* (2013.01); *A61F 2/4684* (2013.01); *A61B 17/1746* (2013.01); *A61F 2002/30471* (2013.01); *A61F 2002/30538* (2013.01); *A61F 2002/30616* (2013.01);
(Continued)

(58) Field of Classification Search
CPC ..... A61B 17/58; A61B 2/34; A61B 17/1746
USPC .............................. 606/86 R, 87–89, 91, 99
See application file for complete search history.

(56) References Cited

U.S. PATENT DOCUMENTS

| 5,141,512 A | 8/1992 | Farmer et al. |
| 6,623,488 B1 | 9/2003 | Leone, Jr. |

(Continued)

FOREIGN PATENT DOCUMENTS

| EP | 2368530 A1 | 9/2011 |
| EP | 2491873 A2 | 8/2012 |

(Continued)

OTHER PUBLICATIONS

European Search Report, European Application No. 13185995.1-1654, Nov. 27, 2013, 7 pages.

(Continued)

*Primary Examiner* — Christopher Beccia
(74) *Attorney, Agent, or Firm* — Barnes & Thornburg LLP

(57) ABSTRACT

An orthopedic surgical instrument and method for positioning an acetabular prosthetic component in a patient's surgically-prepared acetabulum is disclosed. The orthopedic surgical instrument has a base configured to engage the patient's pelvis, a first linkage pivotally coupled to the base, a locking mechanism operable to lock the first linkage in position relative to the base, and a second linkage removably coupled to the first linkage. The second linkage has an alignment axis corresponding to a desired abduction angle and a desired anteversion angle of the acetabular axis of the acetabular prosthetic component.

8 Claims, 15 Drawing Sheets

(51) Int. Cl.
*A61F 2/34* (2006.01)
*A61F 2/30* (2006.01)
*A61B 17/17* (2006.01)

(52) U.S. Cl.
CPC ............... *A61F 2002/4627* (2013.01); *A61F 2002/4629* (2013.01); *A61F 2002/4668* (2013.01); *A61F 2002/4687* (2013.01)

(56) References Cited

U.S. PATENT DOCUMENTS

| | | | |
|---|---|---|---|
| 7,419,492 | B2 | 9/2008 | Yoon et al. |
| 8,764,758 | B2 | 7/2014 | Echeverri |
| 2006/0184177 | A1* | 8/2006 | Echeverri ........... A61B 17/1746 606/91 |
| 2008/0269757 | A1* | 10/2008 | McMinn ................ A61B 17/15 606/87 |
| 2009/0306679 | A1 | 12/2009 | Murphy |
| 2011/0092979 | A1* | 4/2011 | Bartelme ............... A61F 2/4609 606/91 |
| 2011/0276100 | A1 | 11/2011 | Birkbeck et al. |
| 2012/0071802 | A1* | 3/2012 | Reiley ................ A61B 17/1739 602/1 |
| 2012/0190971 | A1* | 7/2012 | de Wekker ......... A61B 19/5244 600/424 |

FOREIGN PATENT DOCUMENTS

| | | |
|---|---|---|
| GB | 2448740 A | 10/2008 |
| WO | 2009058319 A1 | 5/2009 |
| WO | 2010128320 A1 | 11/2010 |

OTHER PUBLICATIONS

Murray, D. W., The Definition and Measurement of Acetabular Orientation, The Journal of Bone and Joint Surgery, Nuffield Orthopaedic Centre, pp. 228-232, vol. 75-B, No. 2, Mar. 1993, Oxford, England.

Tokunaga, Kunihiko, MD et al., Patient-Specific Mechanical Navigation System Addresses Hip Replacement Problems, Orthopedics Today, Jan. 2012, 6 pages.

T. Kalteis et al., Imageless Navigation for Insertion of the Acetabular Component in Total Hip Arthroplasty, Is it as Accurate as CT-Based Navigation?, The Journal of Bone and Joint Surgery (Br), Feb. 2006, pp. 163-167, vol. 88-B, No. 2.

M. Honl et al., Orientation of the Acetabular Component, A Comparison of Five Navigation Systems with Conventional Surgical Technique, The Journal of Bone and Joint Surgery (Br), Oct. 2006, pp. 1401-1405, vol. 88-B, No. 10.

* cited by examiner

SURGICAL INSTRUMENT AND METHOD OF POSITIONING AN ACETABULAR PROSTHETIC COMPONENT

This application is a divisional application of, and claims priority to U.S. patent application Ser. No. 13/786,845, now U.S. Pat. No. 9,055,975, which was filed on Mar. 6, 2013, which claims priority under 35 U.S.C. §119 to U.S. Patent App. Ser. No. 61/707,904 filed Sep. 29, 2012, which is incorporated in its entirety herein.

TECHNICAL FIELD

The present disclosure relates generally to orthopaedic surgical instruments and, more particularly, to surgical instruments used to trial and install an acetabular prosthetic component.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or liner coupled to the shell and configured to engage the femoral head. The femoral head prosthetic component and inner liner of the acetabular component form a ball and socket joint that approximates the natural hip joint.

To facilitate the replacement of the natural joint with a prosthetic hip joint, orthopaedic surgeons may use a variety of orthopaedic surgical instruments such as, for example, reamers, drill guides, drills, positioners, and/or other surgical instruments.

SUMMARY

According to one aspect, a method of positioning an acetabular prosthetic component in a patient's surgically-prepared acetabulum is disclosed. The method includes moving a first linkage relative to a base attached to the patient's pelvis to align the first linkage with the patient's vertical axis when the patient is in a standing position, locking the first linkage in position relative to the base, and securing a second linkage to the first linkage when the patient is in a recumbent position. The second linkage has an alignment axis corresponding to a desired abduction angle and a desired anteversion angle of the acetabular axis of the acetabular prosthetic component. The method also includes attaching the acetabular prosthetic component to the second linkage such that the acetabular axis of the acetabular prosthetic component is parallel with the alignment axis of the second linkage, and advancing the acetabular prosthetic component into the patient's surgically-prepared acetabulum to position the acetabular prosthetic component in the patient's surgically-prepared acetabulum at the desired abduction angle and the desired anteversion angle.

In some embodiments, the method may include attaching the base to the patient's pelvis when the patient is in the standing position. In some embodiments, the method may also include removing the base from the patient's pelvis after locking the first linkage in position relative to the base, and reattaching the base to the patient's pelvis when the patient is in the recumbent position.

In some embodiments, attaching the base to the patient's pelvis when the patient is in the standing position may include engaging the base with at least three locations on the patient's pelvis. Additionally, in some embodiments, the at least three locations on the patient's pelvis may include a point on the patient's superior anterior iliac spine and a point on the patient's pubic tubercle.

In some embodiments, attaching the base to the patient's pelvis when the patient is in the standing position may include applying a predetermined force to the base. In some embodiments, the predetermined force may be approximately 10 lbs-force.

Additionally, in some embodiments, moving the first linkage relative to the base may include moving a bubble to a position in a vial of a bubble level indicator corresponding to plumb.

In some embodiments, the method may include adjusting a first arm of the second linkage to change the abduction angle to the desired abduction angle. The method may also include adjusting a second arm of the second linkage relative to the first arm to change the anteversion angle to the desired anteversion angle.

In some embodiments, the method may include selecting the second linkage from a plurality of second linkages. In some embodiments, advancing the acetabular prosthetic component into the patient's surgically-prepared acetabulum may include operating a parallelogram linkage of the second linkage. Additionally, in some embodiments, the acetabular axis of the acetabular prosthetic component may remain parallel with the alignment axis of the second linkage while the acetabular prosthetic component is advanced into the patient's surgically-prepared acetabulum.

In some embodiments, the recumbent position may be the right lateral decubitus position. In some embodiments, the recumbent position may be the left lateral decubitus position. Additionally, in some embodiments, the recumbent position may be the supine position.

According to another aspect, an orthopaedic surgical instrument for positioning an acetabular prosthetic component in a patient's surgically-prepared acetabulum is disclosed. The instrument includes a base including a plurality of mounting legs configured to engage the patient's pelvis, a first linkage pivotally coupled to the base that includes a spirit level, a locking mechanism operable to lock the first linkage in position relative to the base, and a second linkage removably coupled to the first linkage. The second linkage has an alignment axis corresponding to a desired abduction angle and a desired anteversion angle of the acetabular axis of the acetabular prosthetic component.

In some embodiments, each mounting leg may include a telescopic shaft and a mounting foot configured to engage the patient's pelvis. Additionally, in some embodiments, the mounting feet may include a pair of mounting feet configured to engage the patient's anterior superior iliac spines of the patient's pelvis and a pair of mounting feet configured to engage the pubic tubercles of the patient's pelvis. In some embodiments, the base may include a frame and each mounting leg is pivotally coupled to the frame.

In some embodiments, the second linkage may include a parallelogram linkage configured to maintain the acetabular axis of the acetabular prosthetic component parallel with the alignment axis of the second linkage.

Additionally, in some embodiments, the instrument may further include a shaft configured to be secured to the acetabular prosthetic component. The shaft may have a longitudinal axis that is coincident with the acetabular axis of the acetabular prosthetic component when the acetabular prosthetic component is secured thereto. The parallelogram linkage may include a mount configured to receive the shaft such that the longitudinal axis extends parallel to the alignment axis.

In some embodiments, the instrument may include a plurality of second linkages. Each second linkage may have an alignment axis different from the alignment axis of every other second linkage. In some embodiments, the second linkage may include a first adjustment mechanism operable to move a first arm of the second linkage such that the alignment axis corresponds to a second abduction angle, and a second adjustment mechanism operable to move the first arm such that the alignment axis corresponds to a second anteversion angle.

In some embodiments, the base may include a first mount positioned on a medial side of the base and a second mount positioned on a lateral side of the base. The first mount and the second mount may be configured to be coupled to the first linkage, and the first linkage may be pivotally coupled to the first mount.

According to another aspect, an orthopaedic surgical instrument for positioning an acetabular prosthetic component in a patient's surgically-prepared acetabulum includes a base configured to engage the patient's pelvis, a first linkage coupled to the base that includes a gravity-based indicator, a locking mechanism operable to lock the first linkage in position relative to the base, and a second linkage coupled to the first linkage. The second linkage has an alignment axis corresponding to a desired abduction angle and a desired anteversion angle of the acetabular axis of the acetabular prosthetic component.

BRIEF DESCRIPTION OF THE DRAWINGS

The detailed description particularly refers to the following figures, in which.

DETAILED DESCRIPTION OF THE DRAWINGS

Figure 1:
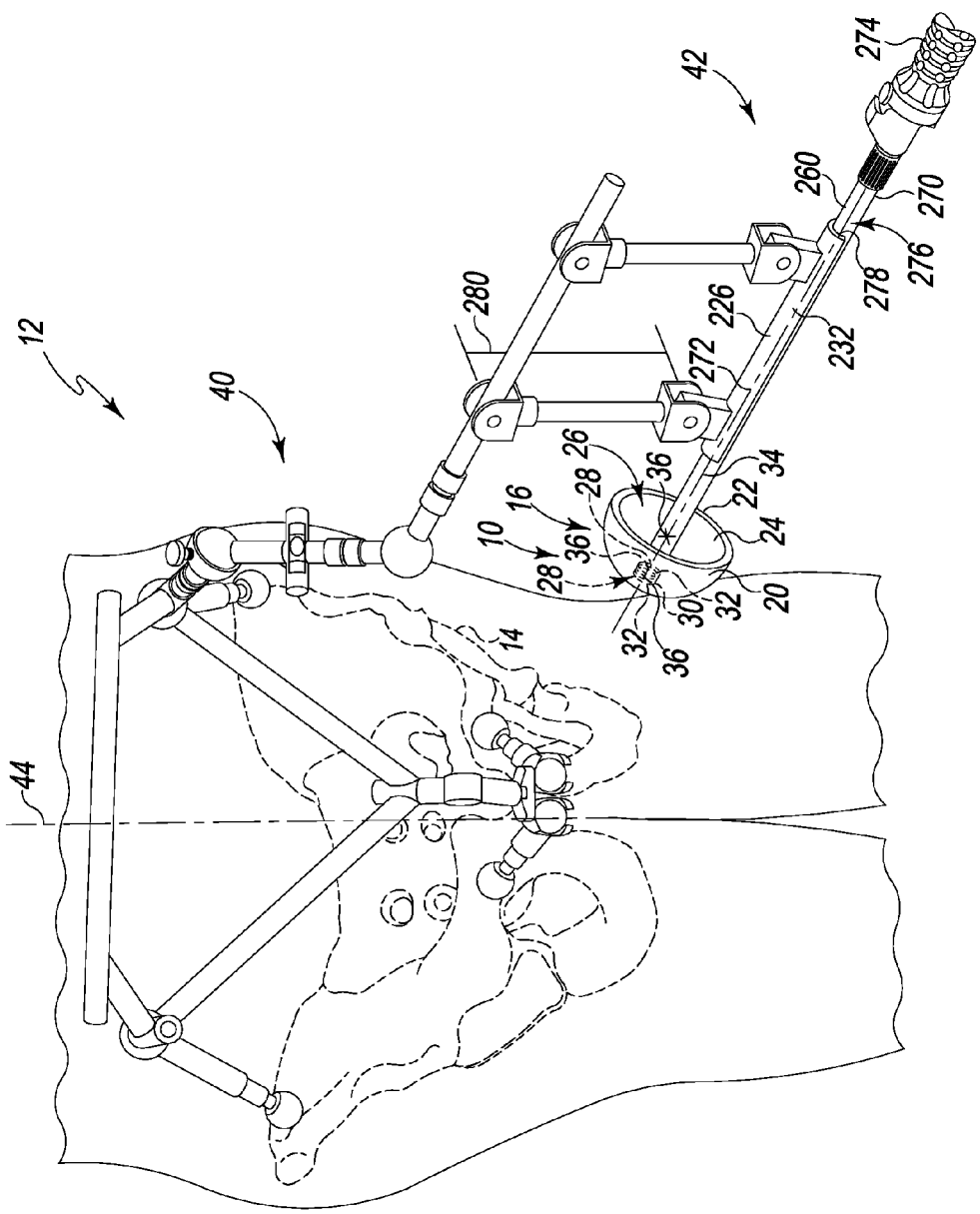
FIG. 1 is a perspective view of an acetabular surgical instrument attached to a patient's body and an acetabular prosthetic component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an acetabular prosthetic component 10 and an orthopaedic surgical instrument 12 (hereinafter instrument 12) are shown. The instrument 12 may be used during a hip arthroplasty surgical procedure to trial and install the acetabular prosthetic component 10 in a patient's pelvic bone 14. It should be appreciated, however, that although the instrument 12 is described below in regard to the performance of a hip arthroplasty surgical procedure, certain concepts associated with the instrument 12 may be utilized in replacement procedures of numerous other joints throughout the body. In other words, one or more of the elements of the instrument 12 may be incorporated into surgical instruments used in, for example, knee, spinal, shoulder, or other replacement procedures.

The acetabular prosthetic component 10 includes an acetabular shell component 16 configured to be implanted within a surgically-prepared acetabulum 18 (see FIG. 7) of the patient's pelvic bone 14. The acetabular shell component 16 includes an outer surface 20 having a convex shape that is hemispherical or partially spherical. The acetabular shell component 16 also includes an annular face 22 and an inner surface 24 having a concave shape that is partially spherical in shape extends inwardly from the face 22. The inner surface 24 defines a cavity 26 in the acetabular shell component 16 that is sized to receive a metallic or polymeric insert.

The acetabular shell component 16 has a passageway 28 defined therein. The passageway 28 is defined by a cylindrical inner wall 30. As shown in FIG. 1, the inner wall 30 has a plurality of internal threads 32 defined thereon.

The acetabular prosthetic component 10 has an acetabular axis 34 that extends outwardly from the acetabular shell component 16. The acetabular axis 34 extends through the center 36 of the annular face 22 and the apex of the inner surface 24. As described in greater detail below, the acetabular axis 34 is oriented at a desired abduction or inclination angle α (see FIG. 7) and a desired anteversion angle β (see FIG. 7) when the acetabular prosthetic component 10 is properly positioned in the patient's surgically-prepared acetabulum 18.

The instrument 12 includes a pelvic reference tool 40 and an insertion tool 42 that may be secured to the acetabular prosthetic component 10. As described in greater detail below, a surgeon or other user may use the pelvic reference tool 40 prior to surgery to establish the patient's vertical axis 44. During surgery, the surgeon may use the pelvic reference tool 40 to reproduce the axis 44 after the patient has been placed in a recumbent position on an operating table. When the insertion tool 42 is attached to the pelvic reference tool 40 with the prosthetic component 10, the surgeon may use the pelvic reference tool 40 to guide the insertion of the acetabular prosthetic component 10 into the patient's surgically prepared acetabulum 18.

Figure 2:
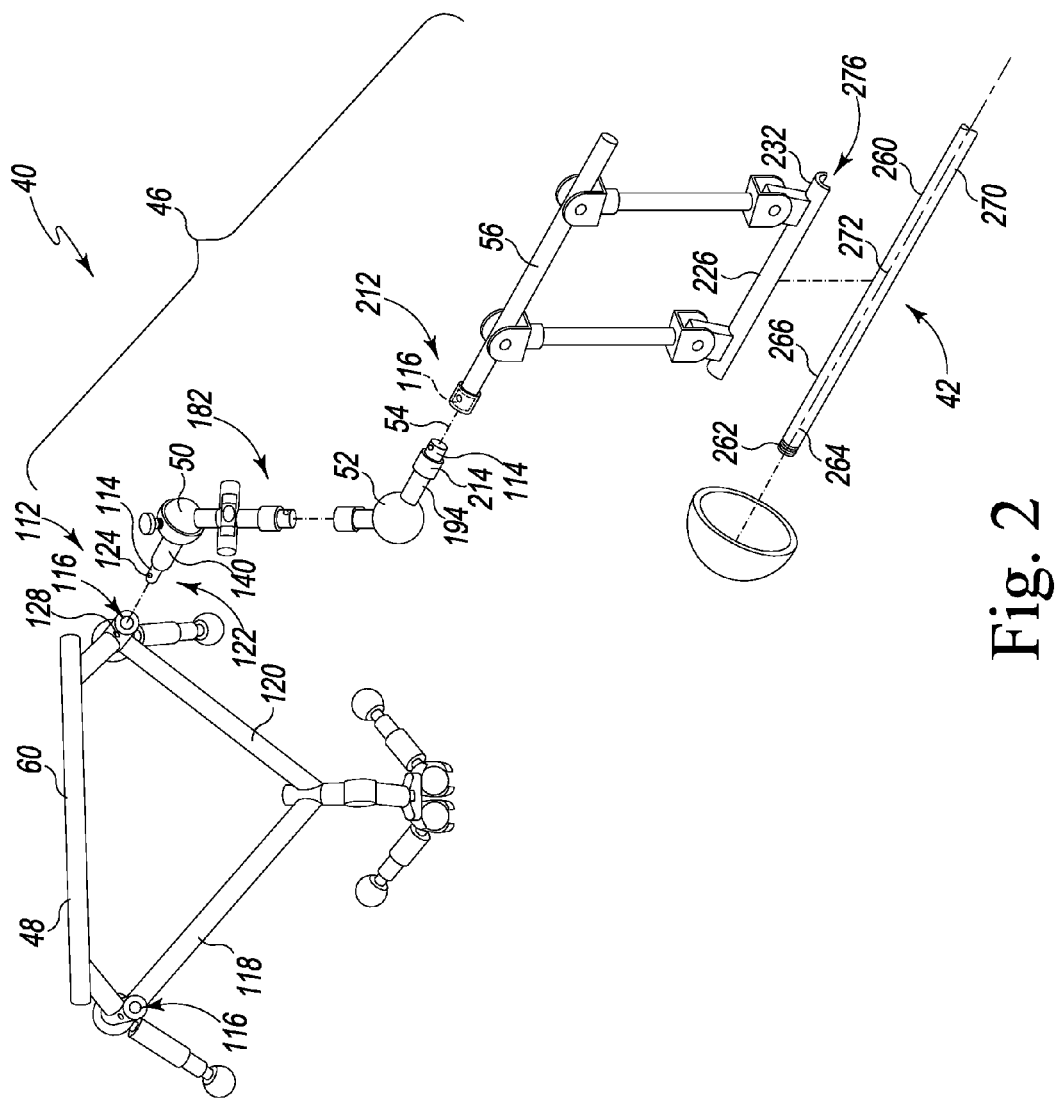
FIG. 2 is an exploded perspective view of the surgical instrument and acetabular prosthetic component of FIG. 1.

Referring now to FIG. 2, the pelvic reference tool 40 includes a number of members 46. The members 46 of the pelvic reference tool 40 include a base member 48 configured to engage the patient's pelvic bone 14 and an indicator linkage 50 operable to establish and reproduce the patient's vertical axis 44. The members 46 also include an alignment device 52 having an alignment axis 54 corresponding to the desired abduction angle and the desired anteversion angle of the acetabular axis 34 of the prosthetic component 10 when the component 10 is properly positioned in the patient's bone 14, as described in greater detail below. The reference tool 40 also has a guide frame 56 configured to be secured to the insertion tool 42. In the illustrative embodiment, the pelvic reference tool 40 may be included in a surgical kit having a plurality of members 46 configured for use with patients of different sizes and/or genders. As such, various members 46 may be detached and replaced as needed during a surgical procedure.

Figure 3:
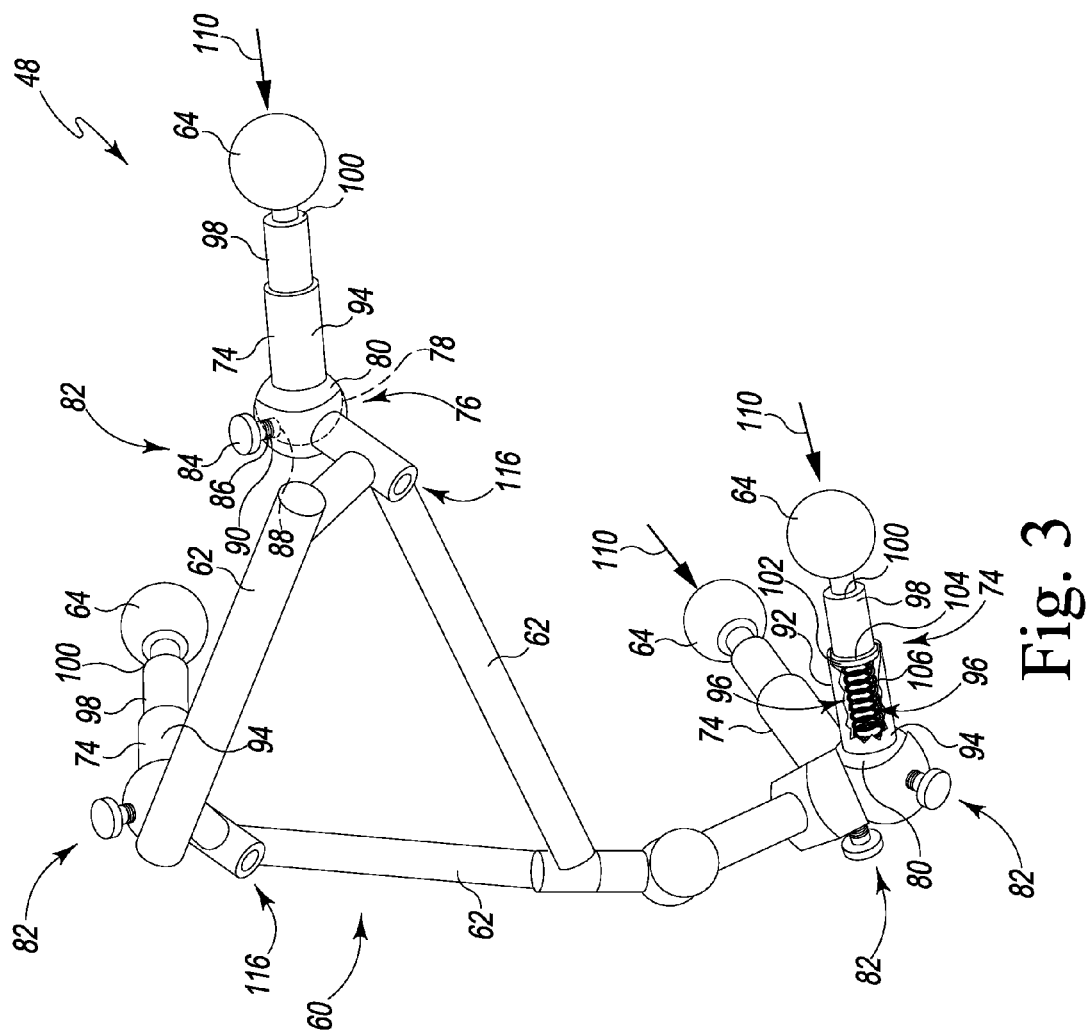
FIG. 3 is a perspective view of a pelvic reference base of the surgical instrument of FIG. 1.

As shown in FIG. 3, the base member 48 includes a frame 60 having a plurality of support beams 62 and a plurality of mounting feet 64 configured to be positioned on the patient's skin in contact with the patient's pelvic bone 14. The mounting feet 64 are sized and oriented to contact the pelvic bone 14 at a plurality of points to establish a reference plane 66 (see FIG. 7) that may be reproduced when the patient is standing or lying on the operating table. In the illustrative embodiment, the mounting feet 64 are configured to contact the superior-anterior iliac spines 68, 70 and the pubic tubercles 72 of the patient's bone 14. It should be appreciated that in other embodiments the mounting feet 64 may be sized and positioned to contact other points on the patient's pelvic bone 14. In the illustrative embodiment, each foot 64 is spherical, but it should be appreciated that in other embodiments one or more of the feet 64 may be a plate, pin, or other structure configured to contact with the patient's pelvic bone 14. It should be appreciated that in other embodiments the each foot may be customized to engage the patient's bone 14 at a unique position and orientation. In such embodiments, each foot may include a customized negative contour that substantially matches the geometry of the patient's bone 14 at the unique position and orientation.

Each mounting foot 64 is secured to a leg 74 extending outwardly from the frame 60. In the illustrative embodiment, each leg 74 is coupled to the frame 60 via a joint 76 such that the leg 74 may be pivoted relative to the frame 60. Each joint 76 is a spheroid joint that includes a socket 78 defined in the frame 60. The leg 74 includes a ball 80 that is received in the socket 78. Each joint 76 permits the corresponding leg 74 to move about an infinite number of axes relative to the frame 60. It should be appreciated that in other embodiments the one or more of the joints may be pin or hinge joints that permit the legs to move about a single axis. It should also be appreciated that in other embodiments the one or more joints may be omitted to fix one ore more of the legs relative to the frame 60.

The base member 48 includes a plurality of locking devices 82 configured to lock the legs 74 in position relative to the frame 60. In the illustrative embodiment, each locking device 82 includes a user-operated knob 84 and a threaded shaft 86. Each threaded-shaft 86 extends through a bore 88 defined in the frame 60. The external threads 90 defined on the shaft 86 are engaged with the internal threads (not shown) of the frame 60. Each knob 84 may be used to rotate its corresponding shaft 86 to move the shaft 86 between an unlocked position and a locked position. In the unlocked position, the shaft 86 is spaced apart from the ball 80 of the leg 74 such that leg 74 may be moved relative to the frame 60; in the locked position, the shaft 86 is engaged with the ball 80, thereby inhibiting movement of the leg 74 relative to the frame 60. It should be appreciated that in other embodiments the locking devices may include any clips, pins, or fasteners to prevent movement of the legs 74.

Each leg 74 of the base member 48 includes a telescopic shaft 92. The telescopic shaft 92 includes a tubular shaft 94 secured to the ball 80. The tubular shaft 94 has an aperture 96 defined therein, and the telescopic shaft 92 includes a rod 98 that extends outwardly from the aperture 96. The rod 98 is configured to extend and retract relative to the tubular shaft 94. As shown in FIG. 3, each mounting foot 64 is secured to an end 100 of each rod 98. Each rod 98 has another end 102 positioned in the aperture 96, and an annular flange 104 extends outwardly therefrom. The annular flange 104 of the rod 98 is configured to engage an inner flange (not shown) of the tubular shaft 94 to prevent the separation of the rod 98 from the tubular shaft 94.

The telescopic shaft 92 includes a biasing element 106 configured to bias the rod 98 in extension such that the annular flange 104 is engaged with the inner flange of the tubular shaft 94. In the illustrative embodiment, the biasing element is a spring 106 positioned in the aperture 96 between the end 102 of the rod 98 and the tubular shaft 94. When a predetermined amount of force is exerted on one of the mounting feet 64 in the direction indicated by arrow 110, the bias exerted by the spring 106 is overcome, and the rod 98 is retracted into the tubular shaft 94. In the illustrative embodiment, the predetermined amount of force is approximately 10 pounds-force.

The support beams 62, legs 74, and mounting feet 64 are formed from a metallic material such as, for example, steel or aluminum. It should be appreciated that in other embodiments one or more of the support beams 62, legs 74, and mounting feet 64 may be formed from a polymeric material. Additionally, in the illustrative embodiment, each support beam 62 is a single monolithic component. It should be appreciated that in other embodiments one or more of the beams may be telescopic such that the length of the beam may be adjusted.

In use, the surgeon may position the base member 48 in contact with the patient's pelvic bone 14. To do so, the surgeon or other user may pivot the legs 74 relative to the frame 60 to align the mounting feet 64 with the superior-anterior iliac spines 68, 70 and the pubic tubercles 72 of the patient's bone 14. When each foot 64 is properly positioned, the corresponding locking device 82 may be utilized to lock the leg 74 in position. The surgeon may then advance the mounting feet 64 into contact with the patient's skin and the bone 14. The surgeon may press on the frame 60 to apply force to the mounting feet 64. When the predetermined amount of force is applied, the biases exerted by the springs 106 are overcome, and the rods 98 retract into the tubular shafts 94 of the legs 74. In other embodiments, the reference tool 40 may include a strap or belt configured to wrap around the patient's body and secure the reference tool 40 to the patient's pelvic bone 14. The strap may be tightened to apply the predetermined amount of force. When the predetermined amount of force is removed, the springs 106 urge the rods 98 to advance out of the tubular shafts 94 to full extension.

As described above, the pelvic reference tool 40 includes an indicator linkage 50 operable to establish and reproduce the patient's vertical axis 44. Returning to FIG. 2, the indicator linkage 50 is configured to be coupled to the base member 48 via a connector 112. In the illustrative embodiment, the connector 112 includes a dowel pin 114 extending from the linkage 50 and a bore 116 defined in the frame 60 of the base member 48. The base member 48 includes a pair of bores 116, with one bore 116 positioned on a medial side 118 of the frame 60 and another bore 116 positioned on the lateral side 120 of the frame 60. In that way, the indicator linkage 50 may be positioned on the medial side 118 or the lateral side 120 of the frame 60 and the pelvic reference tool 40 may be used in a right or left hip arthroplasty procedure.

The connector 112 also includes a detent mechanism 122 configured to maintain the dowel pin 114 in the bore 116. As shown in FIG. 2, the detent mechanism 122 includes a ball 124 extending outward from an aperture (not shown) defined in the dowel pin 114 and a hole or detent 128 defined in the frame 60. When the dowel pin 114 is properly positioned in the bore 116, the ball 124 is received in the detent 126, thereby securing the indicator linkage 50 to the base member 48. The detent mechanism 122 also includes a biasing element (not shown) that biases the ball 124 into position in the detent 128. When a predetermined amount of force is applied to the dowel pin 114, the bias is overcome, and the indicator linkage 50 may be detached from the base member 48. In that way, the detent mechanism 122 permits the surgeon or other user to attach and detach the indicator linkage 50 from the base member 48. It should be appreciated that in other embodiments the connector may include other locking devices or mechanisms to secure the indicator linkage 50 to the base member 48. It should also be appreciated that in other embodiments the indicator linkage 50 may be permanently secured to the base member 48.

Figure 4A:
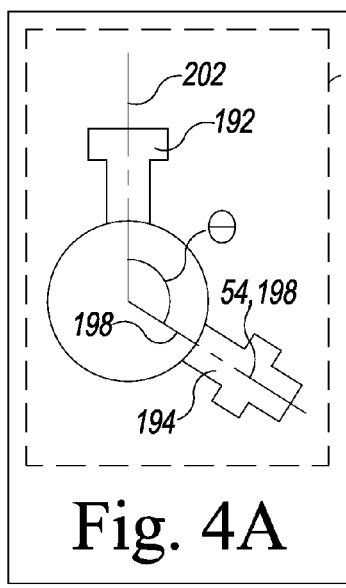
FIG. 4A is an elevation view of the alignment device of FIG. 4 in one reference plane.
Figure 4B:
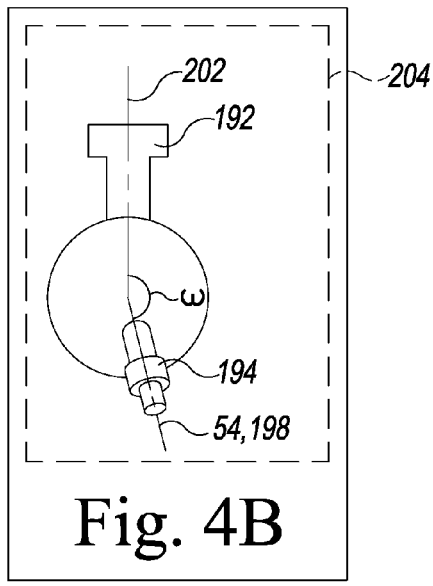
FIG. 4B is an elevation view of the alignment device of FIG. 4 in another reference plane.
Figure 4:
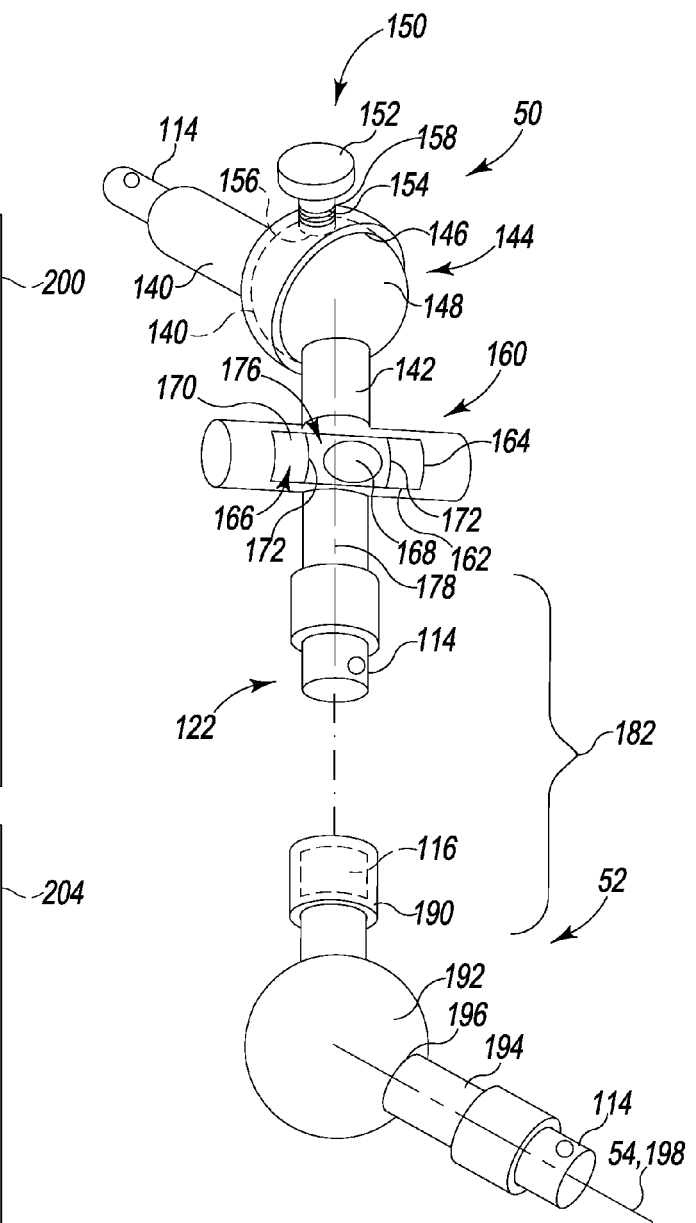
FIG. 4 is a perspective view of an indicator linkage and one embodiment of an alignment device of the surgical instrument of FIG. 1.

Referring now to FIG. 4, the dowel pin 114 of the indicator linkage 50 extends from an upper arm 140. The indicator linkage 50 also includes a lower arm 142 coupled to the upper arm 140. In the illustrative embodiment, the upper arm 140 is coupled to the lower arm 142 via a joint 144. The joint 144 is a spheroid joint that includes a socket 146 defined in the upper arm 140. The lower arm 142 includes a ball 148 that is received in the socket 146. The joint 144 permits the lower arm 142 to move about an infinite number of axes relative to the upper arm 140, which is fixed in position when the indicator linkage 50 is secured to the base member 48. It should be appreciated that in other embodiments the joint may be a pin or hinge joint that permits the lower arm 142 to move about a single axis. It should also be appreciated that in other embodiments the joint may be omitted and the lower arm 142 may be fixed in position relative to the upper arm 140.

The indicator linkage 50 also includes a locking device 150 configured to lock the lower arm 142 in position relative to the upper arm 140. In the illustrative embodiment, the locking device 150 includes a user-operated knob 152 and a threaded shaft 154. Each threaded-shaft 154 extends through a bore 156 defined in the upper arm 140. The external threads 158 defined on the shaft 154 are engaged with the internal threads (not shown) of the upper arm 140. The knob 152 may be used to rotate the shaft 154 to move the shaft 154 between an unlocked position and a locked position. In the unlocked position, the shaft 154 is spaced apart from the ball 148 such that the lower arm 142 is permitted to move relative to the upper arm 140; in the locked position, the shaft 154 is engaged with the ball 148, thereby inhibiting movement of the lower arm 142 relative to the upper arm 140. It should be appreciated that in other embodiments locking devices may include any clips, pins, or fasteners to prevent movement of the lower arm 142.

The lower arm 142 of the indicator linkage 50 includes a gravity-based indicator 160. As used herein, a "gravity-based indicator" is a sensor that indicates position based on gravity. In the illustrative embodiment, the gravity-based indicator 160 is a bubble indicator 162. It should be appreciated that in other embodiments that indicator linkage 50 may include other indicators or sensors to determine the position of the linkage relative to the ground. The bubble indicator 162 includes an oblong-shaped vial 164 that defines a chamber 166 filled with a fluid such as, for example, isopropyl alcohol. As shown in FIG. 4, a bubble 168 is trapped within the chamber 166. Gravity and the physical difference between the gas of the bubbles 168 and the fluid in the chamber 166, respectively, control the function of the bubble indicator 162, with the bubble 168 floating toward the high side of the vial 164.

The vial 164 of the bubble indicator 162 has a face plate 170 that is substantially transparent. In that way, a user may look through the face plate 170 to determine the position of the bubble 168. As shown in FIG. 4, the bubble indicator 162 has a plurality of markings 172 etched into the face plate 170. Each of the markings 172 indicates a predetermined position of the indicator linkage 50. For example, in the illustrative embodiment, the bubble 168 is positioned in a region 176 between the markings 172 when the longitudinal axis 178 of the lower arm 142 is plumb, i.e., perpendicular to the ground.

As described above, the pelvic reference tool 40 also includes an alignment device 52 having an alignment axis 54 corresponding to a desired abduction angle $\alpha$ and a desired anteversion angle $\beta$ of the acetabular axis 34 of the prosthetic component 10 when the component 10 is properly positioned in the patient's bone 14. As used herein, the phrase of one axis corresponding to another refers to an axis that extends parallel to, but is offset from, another axis. The alignment device 52 is configured to be coupled to the indicator linkage 50 via a connector 182. In the illustrative embodiment, the connector 182, like the connector 112, includes a dowel pin 114 that is received in a bore 116 and a detent mechanism 122 configured to maintain the dowel pin 114 in the bore 116. As a result, the connector 182 permits the surgeon or other user to attach and detach the alignment device 52 from the indicator linkage 50. As shown in FIG. 4, the dowel pin 114 extends from the lower arm 142 of the indicator linkage 50 and the bore 116 is defined in the alignment device 52.

As shown in FIG. 4, the bore 116 of the alignment device 52 is defined in an end 190 of a support arm 192. The alignment device 52 also includes a guide arm 194 that is secured to the opposite end 196 of the support arm 192. In the illustrative embodiment, the alignment axis 54 of the alignment device 52 is coincident with the longitudinal axis 198 of the guide arm 194. When the alignment device 52 is viewed in one reference plane 200, an angle θ is defined between the axis 198 of the guide arm 194 and the longitudinal axis 202 of the support arm 192, as shown in FIG. 4A. When the alignment device 52 is viewed another reference plane 204 extending orthogonal to the reference plane 200, an angle ω is defined between the axis 198 of the guide arm 194 and the axis 202 of the support arm 192, as shown in FIG. 4B. The magnitudes of the angles θ, ω are preset and correspond to the desired abduction angle α and the desired anteversion angle β of the acetabular axis 34 of the prosthetic component 10.

As described above, the reference tool 40 may be packaged in a surgical kit including a plurality of alignment devices 52. The arms 192, 194 of each alignment device 52 may be uniquely oriented such that the magnitudes of the angles α, β of each alignment device 52 are different. It should be appreciated the desired abduction angle and the desired anteversion angle (and hence, the magnitude of angles θ, ω) may be determined using operative, radiographic, or anatomic assessments of the desired orientation of acetabular prosthetic component 10. Exemplary definitions of operative, radiographic, or anatomic assessments may be found in "The Definition and Measurement of Acetabular Orientation" by D. W. Murray, British Editorial Society of Bone and Joint Surgery (1993), which is expressly incorporated herein by reference. The surgical kit may include alignment devices 52 having angles θ, ω selected based on any assessment of the desired orientation. As described in greater detail below in regard to FIGS. 13-16, the positions of the arms 192, 194 may be adjusted to change the angles θ, ω in other embodiments of alignment device.

As described above, the pelvic reference tool 40 also includes a guide frame 56 configured to be secured to the insertion tool 42. Returning to FIG. 2, the guide frame 56 is configured to be coupled to one of the alignment devices 52 via a connector 212. In the illustrative embodiment, the connector 212, like the connectors 112, 182, includes a dowel pin 114 that is received in a bore 116 and a detent mechanism 122 configured to maintain the dowel pin 114 in the bore 116. As a result, the connector 212 permits the surgeon or other user to attach and detach the guide frame 56 from the alignment device 52. The dowel pin 114 extends from the end 214 of the guide arm 194 of the alignment device 52.

Figure 5:
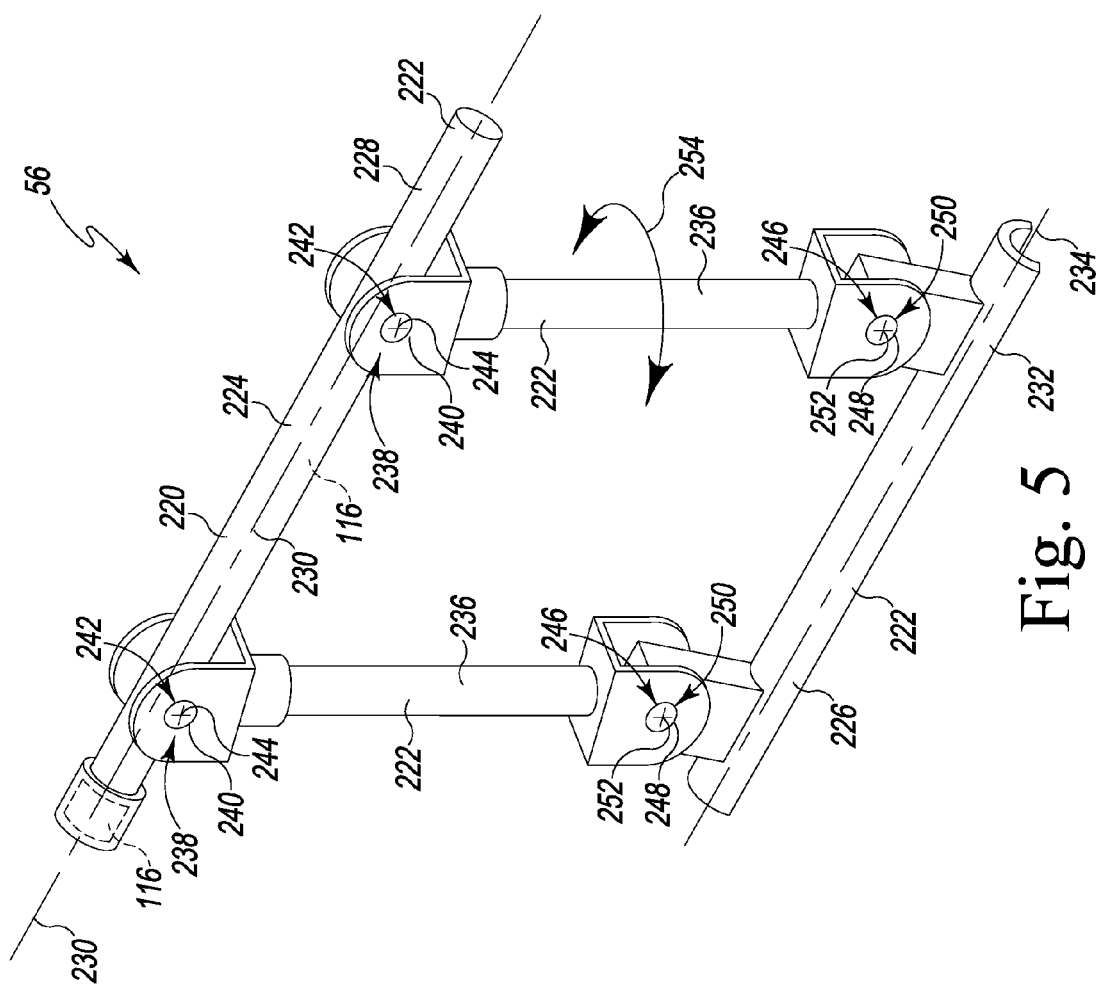
FIG. 5 is a perspective view of a guide frame of the surgical instrument of FIG. 1.

Referring now to FIG. 5, the guide frame 56 is illustratively embodied as a parallelogram linkage 220. The linkage 220 has a plurality of sub-linkages 222, including an upper link 224 that has the bore 116 of the connector 212 defined therein and a lower link 226 configured to receive the insertion tool 42. The upper link 224 includes a shaft 228 having a longitudinal axis 230 that is coincident with the alignment axis 54 of the alignment device 52 when the guide frame 56 is secured to the device 52. The lower link 226 includes a shell 232 having a longitudinal axis 234 that is parallel to the longitudinal axis 230 of the upper link 224.

The upper link 224 is connected to the lower link 226 via a pair of cross links 236. As shown in FIG. 5, each cross link 236 is coupled to the upper link 224 via a joint 238. In the illustrative embodiment, each joint 238 includes a cylindrical pin 240 that is received in bores 242 defined in the corresponding cross link 236 and the upper link 224. The pins 240 define axes 244 about which the cross links 236 are pivoted.

Each cross link 236 is coupled to the lower link 226 via a joint 246. In the illustrative embodiment, each joint 246 includes a cylindrical pin 248 that is received in bores 250 defined in the corresponding cross link 236 and the lower link 226. The pins 248 define axes 252 about which the cross links 236 are pivoted.

In use, the upper link 224 is fixed in position when attached to the alignment device 52. The lower link 226 is configured to move relative to the upper link 224 as indicated by arrows 254, thereby causing the cross links 236 to pivot about the axes 244, 252. The configuration of the sub-linkages 222 ensures that the longitudinal axis 234 of the lower link 226 is parallel to the longitudinal axis 230 of the upper link 224 as the lower link 226 moves relative to the upper link 224.

As described above, the instrument 12 includes an insertion tool 42 that may be secured to the acetabular prosthetic component 10. Returning to FIG. 2, the insertion tool 42 has a shaft 260 that includes a plurality of external threads 262 corresponding to the threads 32 of the acetabular prosthetic component 10. As shown in FIG. 2, the external threads 262 are defined at an end 264 of the shaft 260 such that the acetabular prosthetic component 10 may be threaded onto the end 264 of the shaft 260, thereby coupling the acetabular prosthetic component 10 to the insertion tool 42 for trialing or implantation.

The shaft 260 of the insertion tool 42 has a cylindrical body 266 that extends from the end 264 to an end 270. The shaft 260 defines a longitudinal axis 272 that is coincident with the acetabular axis 34 of the acetabular prosthetic component 10 when the component 10 is secured to the insertion tool 42. As shown in FIG. 1, the insertion tool 42 includes a handle 274 that is coupled to the end 270 of the shaft 260. It should be appreciated that in other embodiments the handle 274 may be omitted.

The lower link 226 of the guide frame 56 is configured to receive the insertion tool 42. In the illustrative embodiment, the shell 232 of the lower link 226 has a passageway 276 defined therein that is sized to receive the shaft 260 of the insertion tool 42. As shown in FIG. 1, when the insertion tool 42 is attached to the guide frame 56, the shaft 260 engages the cylindrical surface 278 of the shell 232. In other embodiments, the guide frame may include a fastener or other locking device to secure the insertion tool to the reference tool 40. It should also be appreciated that in other embodiments the insertion tool may be integrated into the guide frame to form a single assembly.

In the illustrative embodiment, each cross link 236 of the guide frame 56 has a predetermined length 280 to locate the lower link 226 (and hence insertion tool 42) at a predetermined orientation relative to the patient's pelvic bone 14. It should be appreciated that in other embodiments the cross links 236 may be adjustable to vary the length 280 to match a particular patient's anatomy.

The insertion tool 40, indicator linkage 50, alignment device 52, and guide frame 56 are formed from a metallic material such as, for example, steel or aluminum. It should be appreciated that in other embodiments one or more of those tools may be formed from a polymeric material.

Figure 6:
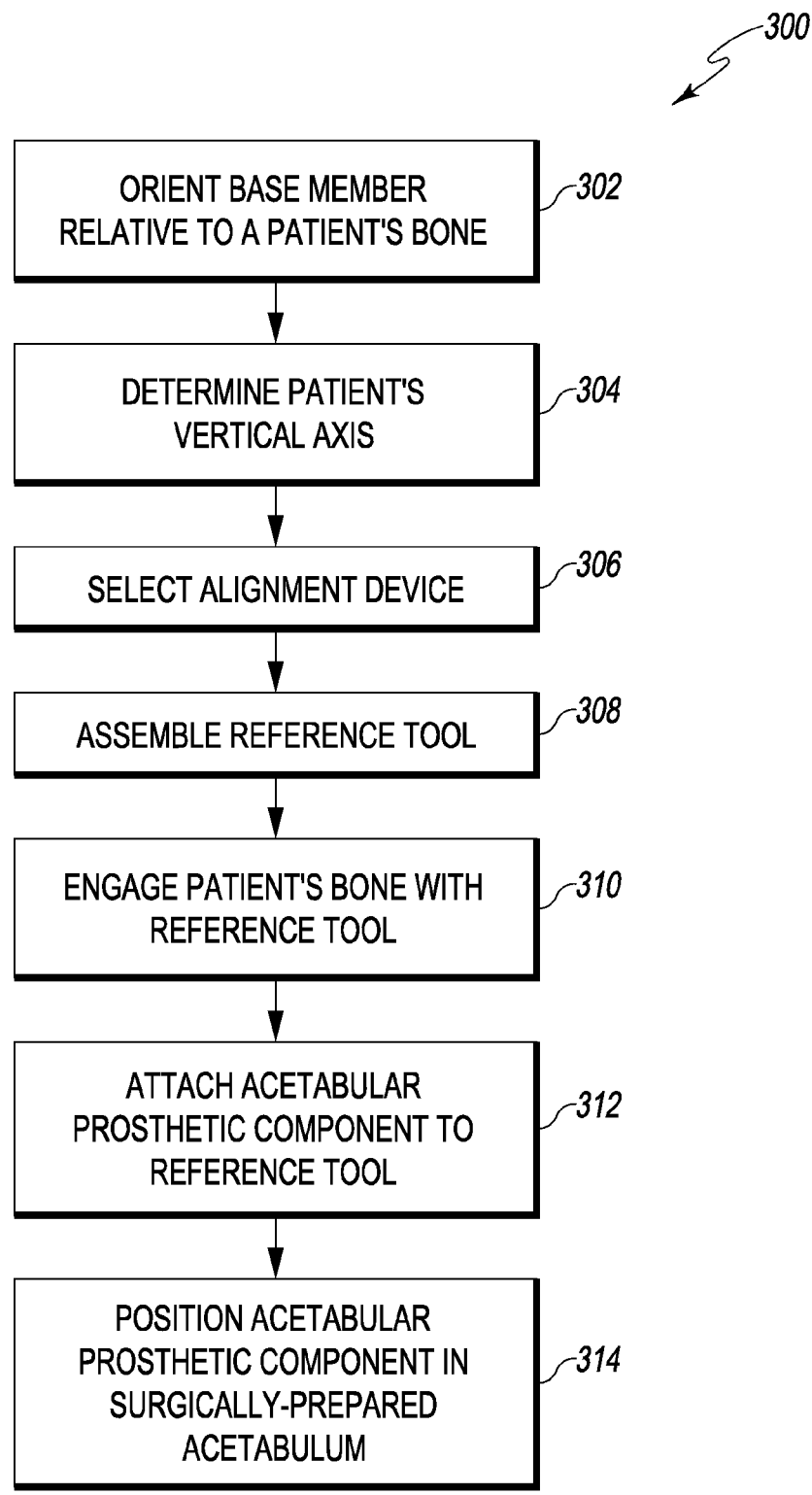
FIG. 6 is a simplified flow chart showing an exemplary method of using the surgical instrument of FIG. 1.
Figure 8:
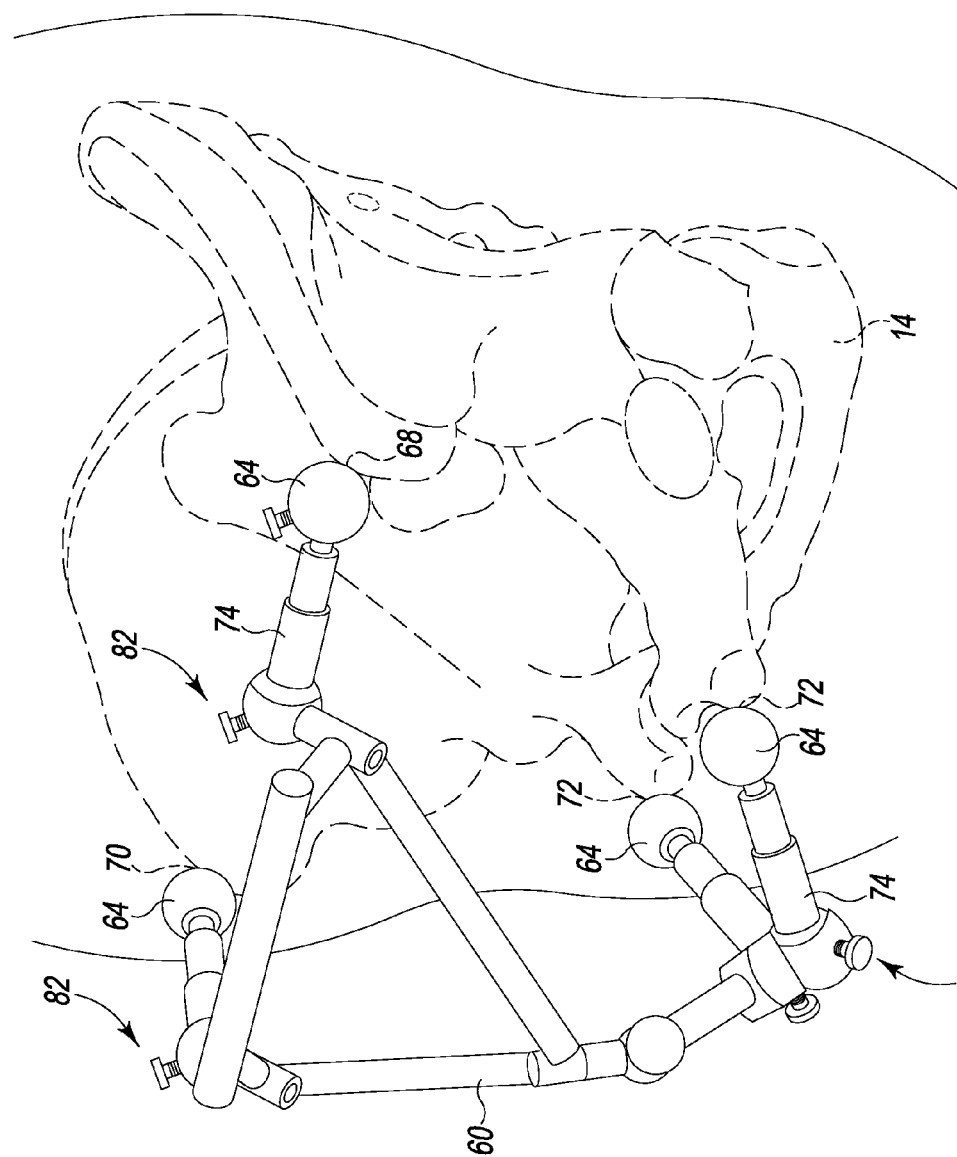
FIG. 8 is a perspective view of the pelvic reference base of the acetabular surgical instrument of FIG. 1 attached to the patient's body when the patient is in a standing position.
Figure 9:
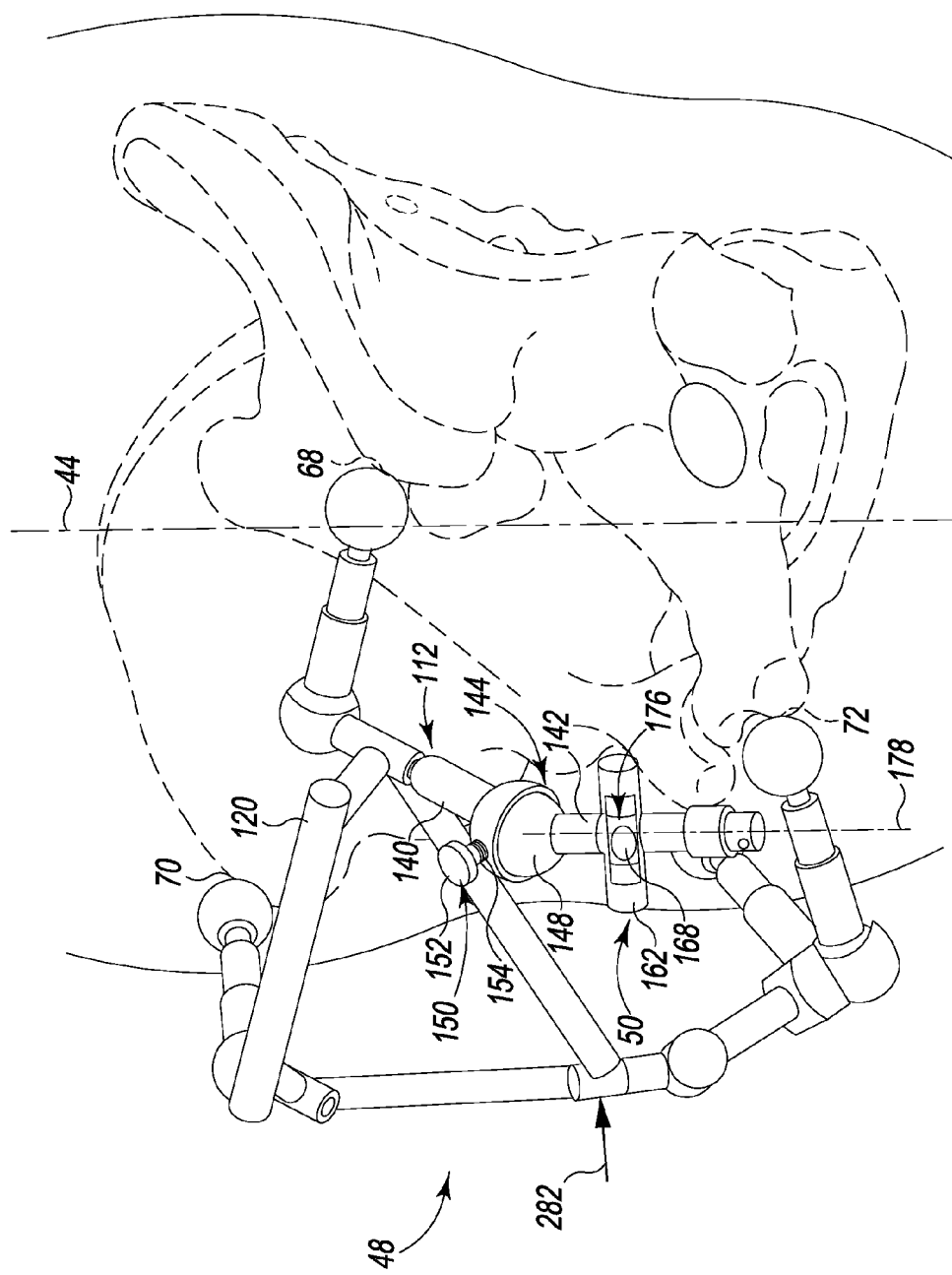
FIG. 9 is a view similar to FIG. 8 of the pelvic reference base and the indicator linkage of the acetabular surgical instrument of FIG. 1 attached to the patient's body.
Figure 10:
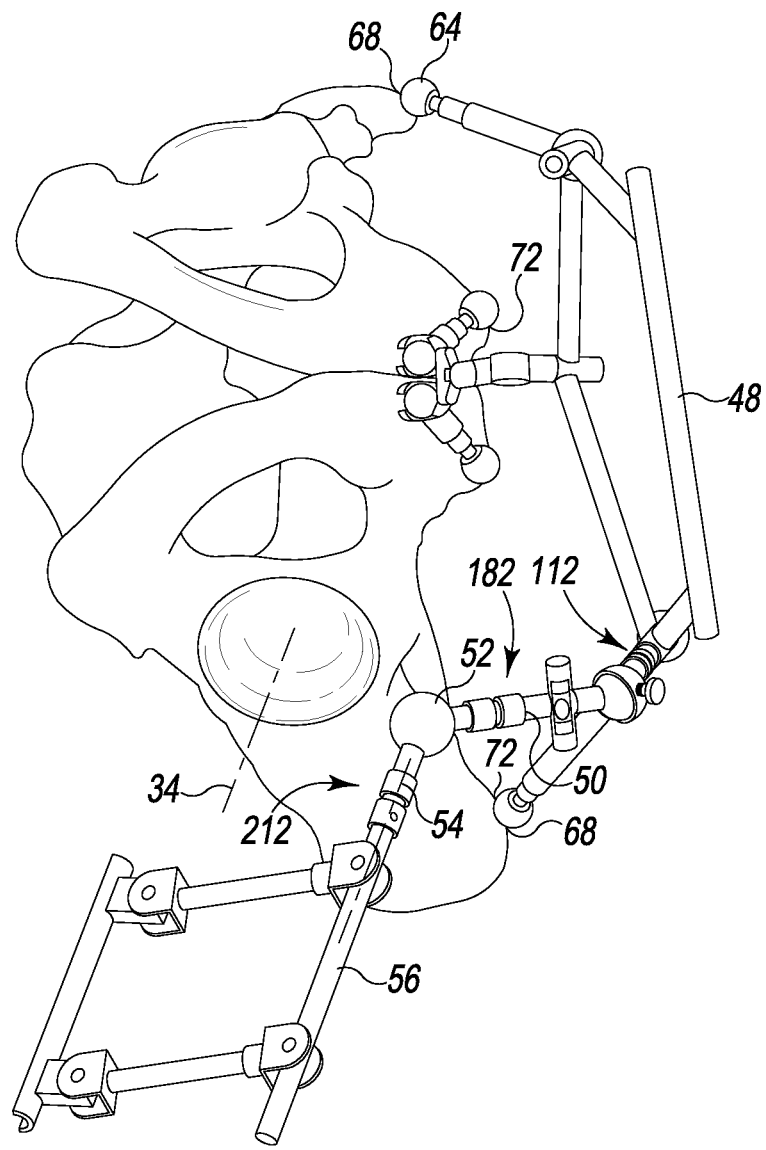
FIG. 10 is a perspective view of the acetabular surgical instrument of FIG. 1 attached to the patient's body when the patient is in a recumbent position.
Figure 11:
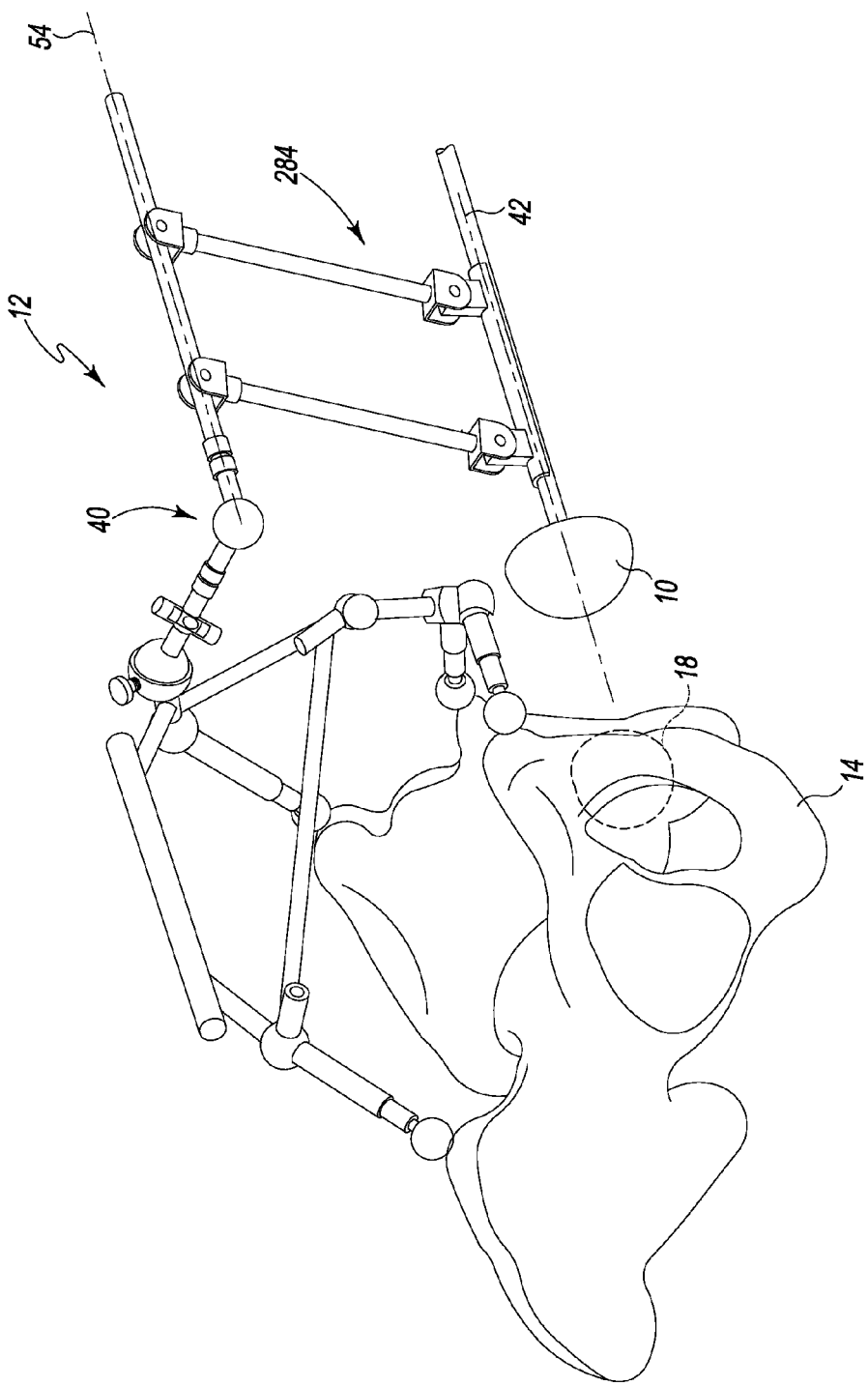
FIG. 11 is another perspective view of the acetabular prosthetic component attached to the acetabular surgical instrument.
Figure 12:
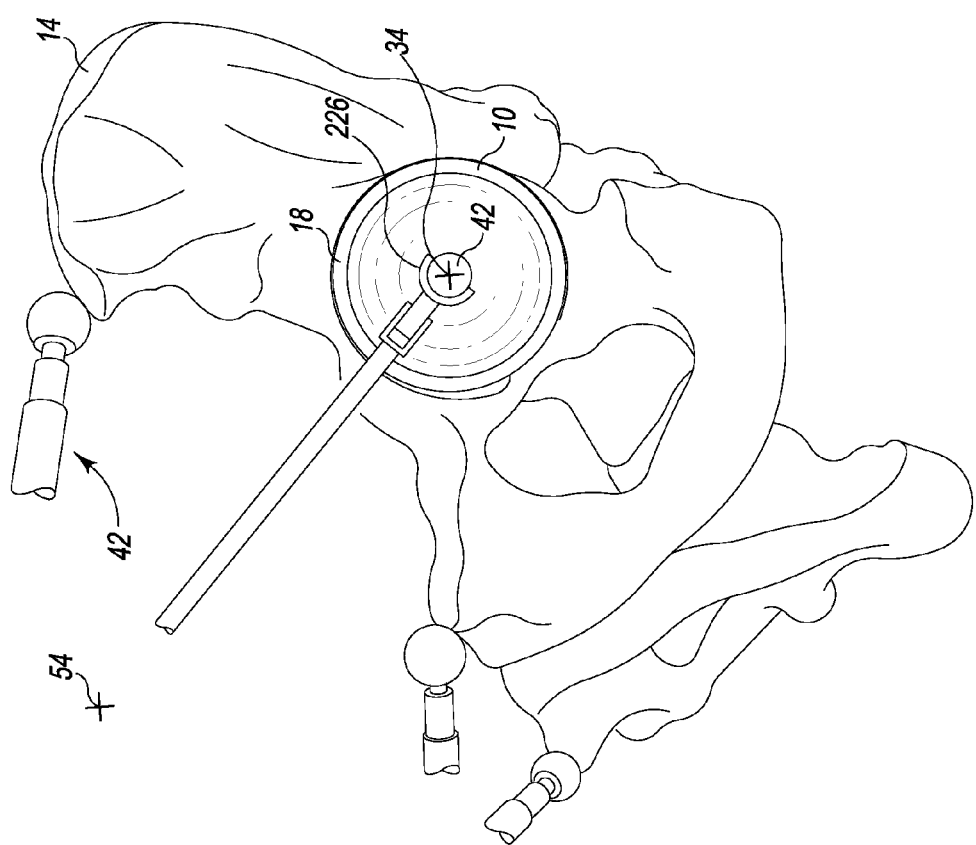
FIG. 12 is another perspective view of the acetabular prosthetic component and the acetabular surgical instrument attached to the patient's body.

In operation, the orthopaedic surgical instrument 12 is utilized to trial and install the acetabular prosthetic component 10 during the performance of an orthopaedic surgical procedure like that shown in FIG. 6. As shown in FIGS. 8 and 9, the pelvic reference tool 40 may be used prior to surgery to establish the patient's vertical axis 44. Thereafter, the pelvic reference tool 40 may be used to reproduce the axis 44 after the patient has been placed in a recumbent position on an operating table, as shown in FIG. 10. As shown in FIGS. 11 and 12, the pelvic reference tool 40 may be used to guide the insertion of the acetabular prosthetic component 10 into the patient's surgically prepared acetabulum 18.

Figure 7:
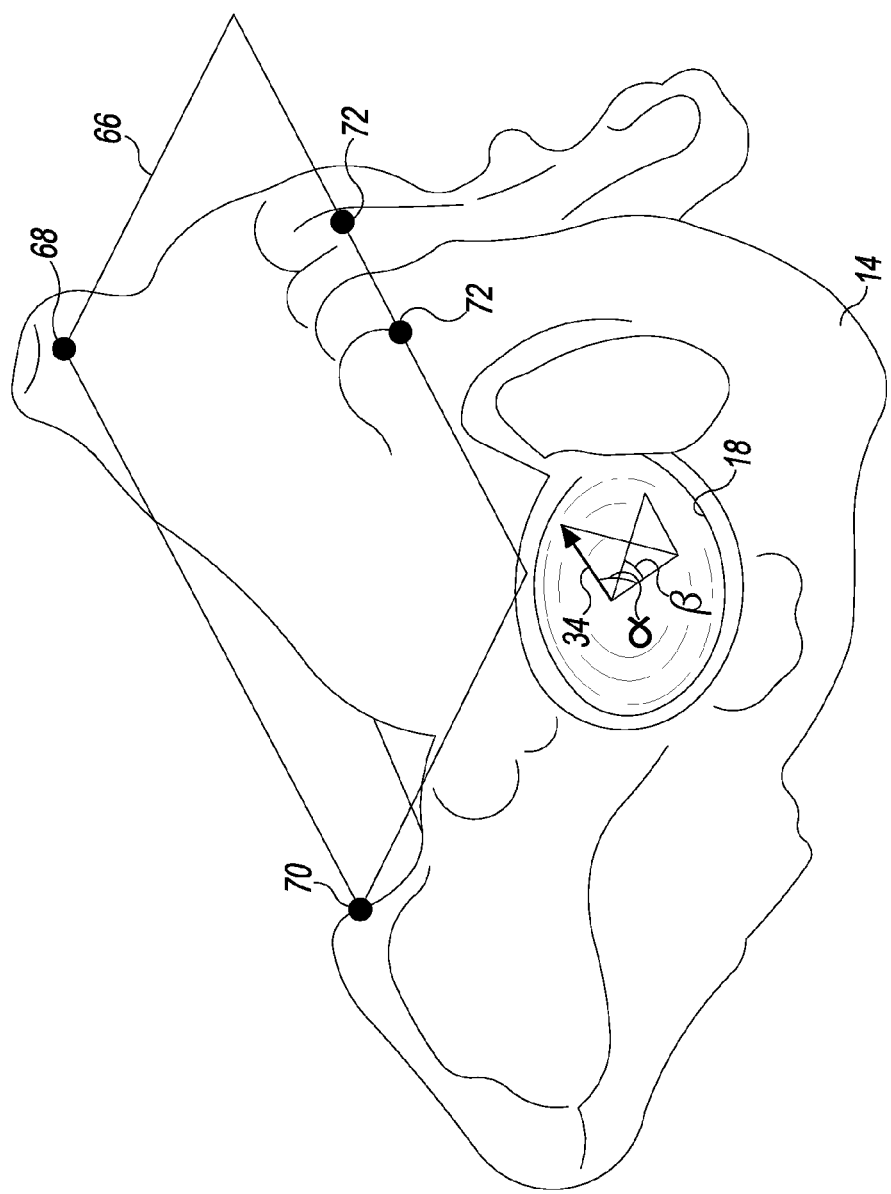
FIG. 7 is a perspective view of a pelvic bone of a patient showing a desired a desired abduction angle and a desired anteversion angle of the acetabular prosthetic component.

Referring now to FIG. 6, an illustrative orthopaedic surgical procedure 300 using the component 10 is shown. In block 302 of the procedure 300, the base member 48 of the reference tool 40 relative to the patient's pelvic bone 14 to establish the plane 66. As shown in FIG. 7, the superior-anterior iliac spines 68, 70 and the pubic tubercles 72 of the patient's bone 14 define a pelvic reference plane 66 that is unique to each patient. The base member 48 is oriented relative to the patient's bone 14 such that each mounting foot 64 is positioned over one of the superior-anterior iliac spines 68, 70 and the pubic tubercles 72.

To do so, the surgeon or other user may pivot the legs 74 of the base member 48 relative to the frame 60 to align the mounting feet 64 with the superior-anterior iliac spines 68, 70 and the pubic tubercles 72 of the patient's bone 14. When each foot 64 is properly positioned, the corresponding locking device 82 may be utilized to lock the leg 74 in position. The surgeon may then advance the mounting feet 64 into contact with the patient's skin and the bone 14, as shown in FIG. 8.

The surgeon may attach the indicator linkage 50 to the base member 48 before or after the base member 48 is positioned on the patient's pelvic bone 14. As described above, the indicator linkage 50 may be positioned on the medial side 118 or the lateral side 120 of the frame 60 and the pelvic reference tool 40 may be used in a right or left hip arthroplasty procedure. In the illustrative embodiment, a left hip arthroplasty procedure is performed and the indicator linkage 50 is attached to the lateral side 120 of the frame 60.

To attach the indicator linkage 50 to the base member 48, the dowel pin 114 of the connector 112 is aligned with the bore 116 defined in the frame 60 of the base member 48. The dowel pin 114 is then advanced into the bore 116. When the dowel pin 114 is properly positioned in the bore 116, the ball 124 of the detent mechanism 122 is received in the detent 126, thereby securing the indicator linkage 50 to the base member 48.

Returning to FIG. 6, the procedure 300 may advance to block 304 in which the patient's vertical axis 44 is determined. To do so, the patient is placed in a standing position. In the illustrative embodiment, the patient is placed in a position in which the patient's spine, as indicated by axis 44 in FIGS. 1 and 9, is perpendicular to the ground. The surgeon may press on the frame 60 in the direction indicated by arrow 282 in FIG. 9 to apply force to the mounting feet 64 while the patient is standing. When the predetermined amount of force is applied, the biases exerted by the springs 106 are overcome, and the rods 98 retract into the tubular shafts 94 of the legs 74.

With the rods 98 in the retracted position and the patient standing, the surgeon may pivot the lower arm 142 of the indicator linkage 50 about the joint 144. As described above, the joint 144 permits the lower arm 142 to move about an infinite number of axes relative to the upper arm 140, which is fixed in position when the indicator linkage 50 is secured to the base member 48. With the patient in the standing position, the surgeon may move the lower arm 142 about the joint 144 until the bubble 168 of the indicator 162 is positioned in the region 176 between the markings 172. As described above, that position indicates when the longitudinal axis 178 of the lower arm 142 is plumb or perpendicular to the ground. In that orientation, the longitudinal axis 178 of the lower arm 142 is parallel to the vertical axis 44 of the patient. The surgeon may then rotate the knob 152 of the locking device 150 to advance the shaft 154 into contact with the ball 148 to inhibit further movement of the lower arm 142 relative to the upper arm 140. The base member 48 and the indicator linkage 50 may then be removed from the patient's bone 14.

It should be appreciated that the activities described in blocks 302 and 304 may be performed prior to surgery during a pre-operative appointment. The surgeon may also perform some or all of the activities described in blocks 302 and 304 multiple times verify the vertical axis 44 of the patient.

The procedure 300 may then advance to block 306 in which an alignment device 52 is selected. As described above, the surgeon may select an alignment device 52 from a plurality of alignment devices 52 that has an alignment axis 54 corresponding to the desired abduction angle α (see FIG. 7) and the desired anteversion angle β (see FIG. 7) of the axis 34 of the acetabular prosthetic component 10 when the component 10 is properly positioned in the patient's bone 14. The arms 192, 194 of each alignment device 52 may be uniquely oriented such that the magnitudes of the angles θ, ω of each alignment device 52 are different. Further, the magnitudes may be determined using operative, radiographic, or anatomic, or other assessments of the desired orientation of acetabular prosthetic component 10. The surgeon may select the alignment device 52 based on, for example, the condition of the patient's bone, the patient's age, the patient's gender, and so forth. After selecting the alignment device 52, the procedure 300 may advance to block 308.

In block 308, the reference tool 40 is assembled. If the indicator linkage 50 had been detached from the base member 48 upon completion of the activities described in regard to blocks 302, 304, the indicator linkage 50 may be reattached to the base member 48 in the manner described above. Additionally, the alignment device 52 may be secured to the indicator linkage 50. To do so, the dowel pin 114 of the connector 182 is aligned with the bore 116 defined in the alignment device 52. The dowel pin 114 is then advanced into the bore 116. When the dowel pin 114 is properly positioned in the bore 116, the ball 124 of the detent mechanism 122 is received in the detent 126, thereby securing the alignment device 52 to the indicator linkage 50.

The guide frame 56 is also secured to the alignment device 52 in a similar manner. The dowel pin 114 of the connector 212 is aligned with the bore 116 defined in the upper link 224 of the guide frame 56. The dowel pin 114 is then advanced into the bore 116. When the dowel pin 114 is properly positioned in the bore 116, the ball 124 of the detent mechanism 122 is received in the detent 126, thereby securing the guide frame 56 to the alignment device 52.

In block 310 of the procedure 300, the reference tool 40 is engaged with the patient's bone 14 while the patient is in a recumbent position on the operating table. As described above, the reference tool 40 may be used in a right or left hip arthroplasty procedure. Thus, the patient may be placed in any recumbent position, including a left lateral decubitus position, a right lateral decubitus position, or a supine position. For example, because a left hip arthroplasty procedure is performed, the patient may be placed in a right lateral decubitus position so that the left hip is facing upward. Prior to engaging the reference tool 40 with the patient's bone 14, various reaming guides, reamers, and other surgical tools may be used to surgically prepare the patient's acetabulum to receive the prosthetic component 10. After the surgically-prepared acetabulum 18 is produced, the reference tool 40 is engaged with the patient's bone 14, as shown in FIG. 10. The surgeon or other user may again align the mounting feet 64 with the superior-anterior iliac spines 68, 70 and the pubic tubercles 72 of the patient's bone 14. When each foot 64 is properly positioned, the surgeon may advance the mounting feet 64 into contact with the patient's skin and the bone 14.

The surgeon may press on the frame 60 to apply force to the mounting feet 64. When the predetermined amount of force is applied, the biases exerted by the springs 106 are overcome, and the rods 98 retract into the tubular shafts 94 of the legs 74. As described above, the reference tool 40 may be used with a strap or belt configured to wrap around the patient's body and secure the reference tool 40 to the patient's pelvic bone 14. The strap may be tightened to apply the predetermined amount of force. It should be appreciated that in other embodiments other fasteners may be used to hold the reference tool 40 in position on the patient's pelvic bone 14. When the pelvic reference tool 40 is properly positioned, the locked indicator linkage 50 of the pelvic reference tool 40 reproduces the vertical axis 44 while the patient is in the recumbent position. Additionally, the alignment axis 54 is positioned offset from the patient's surgically-prepared acetabulum 18. In that position, the alignment axis 54 extends parallel to the desired orientation of the acetabular axis 34 of the prosthetic component 10, as dictated by the desired abduction angle α and desired anteversion angle β.

In block 312, the acetabular prosthetic component 10 is attached to the reference tool 40. To do so, the acetabular prosthetic component 10 may is attached to the insertion tool 42. To do so, the passageway 28 defined in the acetabular shell component 16 is aligned with the shaft 260 of the tool 42. The acetabular shell component 16 may be advanced into contact with the end 264 of the shaft 260 such that the threads 32 of the acetabular shell component 16 engage the threads 262 of the shaft 260. One of the tool 42 and the acetabular shell component 16 may then be rotated relative to the other component to thread the acetabular shell component 16 onto the end 264 of the shaft 260, thereby securing the acetabular prosthetic component 10 to the insertion tool 42.

With the acetabular prosthetic component 10 secured to the insertion tool 42, the surgeon may attach the insertion tool 42 to the reference tool 40, as shown in FIG. 11. As described above, the shell 232 of the lower link 226 of the reference tool 40 has a passageway 276 defined therein that is sized to receive the shaft 260 of the insertion tool 42. As shown in FIG. 11, when the insertion tool 42 is attached to the guide frame 56, the shaft 260 engages the cylindrical surface 278 of the shell 232.

When the insertion tool 42 is attached to the reference tool 40, the longitudinal axis 272 of the tool 42 extends parallel to the alignment axis 54 of the alignment device 52. Additionally, because the acetabular prosthetic component 10 is attached to the insertion tool 42, the acetabular axis 34 of the component 10 also extends parallel to the alignment axis 54 and hence is positioned at the desired abduction angle α and the desired anteversion angle β. As described above, the reference tool 40 or the insertion tool 42 may include one or more fasteners to secure the tools 40, 42 together.

The procedure 300 may advance to block 314 in which the acetabular prosthetic component 10 is inserted into the patient's surgically-prepared acetabulum 18. To do so, the surgeon or other user may grasp the insertion tool 42 by the handle 274. The surgeon then rotate the cross links 236 about the axes 244, 252, as indicated by arrows 284 in FIG. 11, to advance to the acetabular prosthetic component 10 toward the patient's pelvic bone 14 and into the patient's surgically-prepared acetabulum 18. Because the acetabular axis 34 of the component 10 extends parallel to the alignment axis 54 of the alignment device 52, the component 10 is positioned at the desired abduction angle α and the desired anteversion angle β.

While the instrument 12 is used with the acetabular prosthetic component 10 in the procedure outlined above, the instrument 12 may also be used with an acetabular prosthetic trial component. When attached to a trial component, the user may use the instrument 12 to determine the type, configuration, and installed position of the acetabular prosthetic component that is to be implanted.

Figure 13:
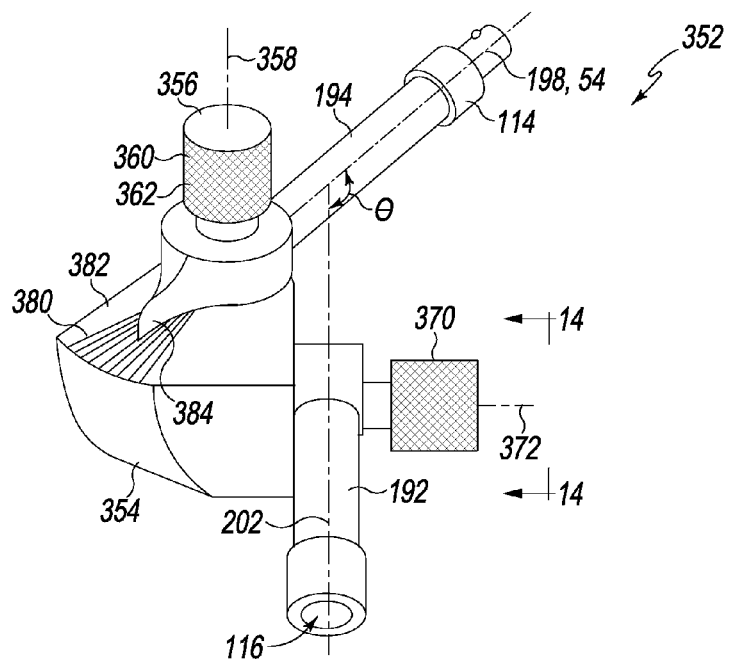
FIG. 13 is a perspective view of another embodiment of an alignment device for the surgical instrument of FIG. 1.
Figure 14:
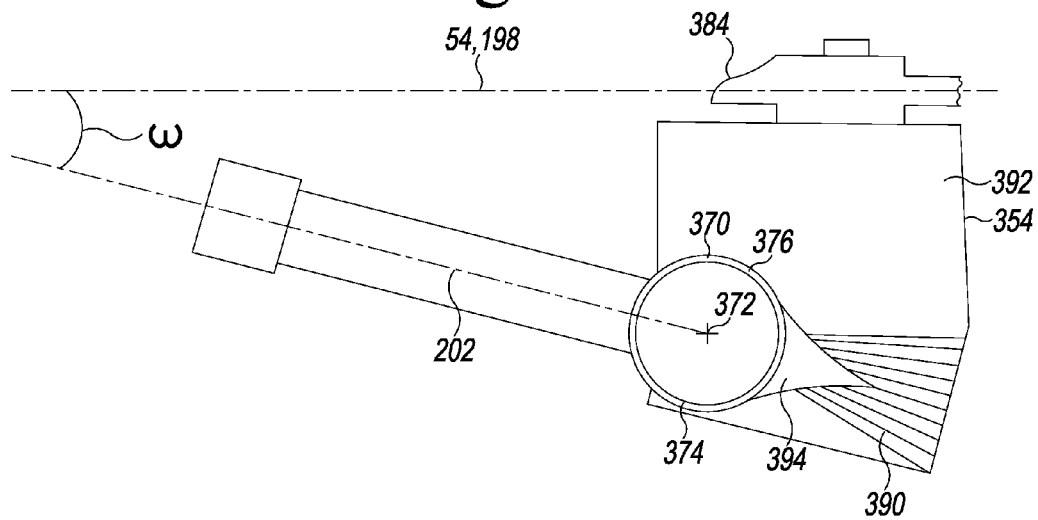
FIG. 14 is an elevation view of the alignment device as indicated by the line 14-14 in FIG. 13.

In other embodiments, a surgeon may desire to adjust the abduction angle and the anteversion angle intraoperatively. As shown in FIGS. 13 and 14, another embodiment of an alignment device (hereinafter alignment device 352) is shown that permits the surgeon to change the abduction angle and the anteversion angle. Some features of the embodiment illustrated in FIGS. 13 and 14 are substantially similar to those discussed above in reference to the embodiment of FIGS. 1-12. Such features are designated in FIGS. 13 and 14 with the same reference numbers as those used in FIGS. 1-12.

Referring now to FIG. 13, the alignment device 352 includes a support arm 192 and a bore 116 defined therein. Similar to alignment device 52, the dowel pin 114 of the indicator linkage 50 is received in the bore 116 such that the alignment device 352 may be secured to the indicator linkage 50. The alignment device 352 includes a dowel pin 114 extending from the guide arm 194. As described above, the dowel pin 114 is configured to be received in a bore 116 defined in the upper link 224 of the guide frame 56 such that the alignment device 352 may be secured to the guide frame 56.

The guide arm 194 of the alignment device 352 has a longitudinal axis 198. The longitudinal axis 198 is coincident with the alignment axis 54 of the alignment device 352. When the alignment device 352 is viewed in one reference plane, an angle θ is defined between the axis 198 of the guide arm 194 and the longitudinal axis 202 of the support arm 192, as shown in FIG. 13. When the alignment device 352 is viewed another reference plane, an angle ω is defined between the axis 198 of the guide arm 194 and the axis 202 of the support arm 192, as shown in FIG. 14.

The arms 192, 194 of the alignment device 352 are pivotally coupled to a hub 354. The alignment device 352 includes a user-operated adjustment mechanism 356 that is operable to pivot the arm 194 about an axis 358. As shown in FIG. 13, the adjustment mechanism 356 includes a knob 360 having a knurled grip 362. In use, the user may grasp the grip 362 to rotate the knob 360 about the axis 358, thereby changing the magnitude of the angle θ defined between the axis 198 of the guide arm 194 and the axis 202 of the support arm 192.

The alignment device 352 also includes a user-operated adjustment mechanism 370 that is operable to pivot the arm 192 about an axis 372. As shown in FIG. 14, the adjustment mechanism 356 includes a knob 374 having a knurled grip 376. In use, the user may grasp the grip 376 to rotate the knob 374 about the axis 372, thereby changing the magnitude of angle ω defined between the axis 198 of the guide arm 194 and the axis 202 of the support arm 192.

The alignment device 352 has a plurality of markings 380, which are etched into an outer surface 382 of the hub 354. Each of the markings 380 indicates a predetermined abduction angle α of the acetabular prosthetic component 10 within the patient's surgically-prepared acetabulum 18. The guide arm 194 has a pointer 384 that may be aligned with one of the markings 380 to indicate the selected abduction angle α.

As shown in FIG. 14, the alignment device 352 also has a plurality of markings 390, which are etched into an outer surface 392 of the hub 354. Each of the markings 390 indicates a predetermined anteversion angle β of the acetabular prosthetic component 10 within the patient's surgically-prepared acetabulum 18. The support arm 192 has a pointer 394 that may be aligned with one of the markings 390 to indicate the selected anteversion angle β. In the illustrative embodiment, the markings 380, 390 include a plurality of numerical indicators 400 that are associated with angles α, β.

The reference tool 40 may be packaged in a surgical kit including a plurality of alignment devices 352. Each alignment device 352 may be configured for use with the left or right hip. Additionally, the It should be appreciated the abduction angles α and the anteversion angles β indicated by markings 380, 390 may be determined using operative, radiographic, anatomic, or other assessments of the desired orientation of acetabular prosthetic component 10. The surgical kit may include alignment devices 52 having markings 380, 390 positioned on the hub 354 based on any of those assessments of the desired orientation.

In use, the surgeon may select one of alignment devices 352. The surgeon may then secure the alignment device 352 to the indicator linkage 50 and the guide frame 56 in the manner described above. The surgeon or other user may utilize the knobs 360, 374 to change the magnitudes of the angles θ, ω and hence the desired abduction angle α and the desired anteversion angle β of the axis 34 of the acetabular prosthetic component 10. When the angle adjustments are complete, the surgeon may insert the acetabular prosthetic component 10 into the patient's surgically-prepared acetabulum 18.

Figure 15:
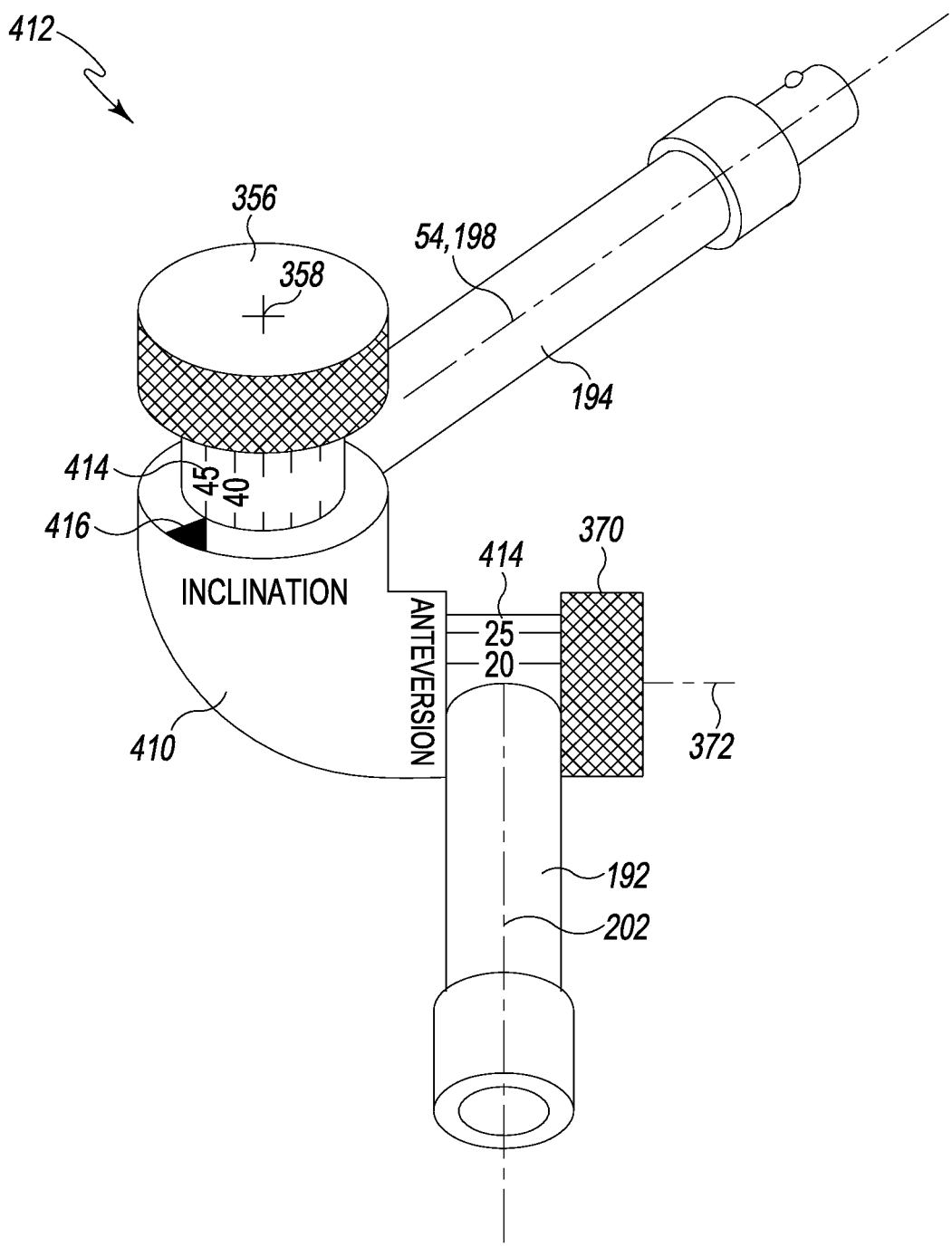
FIG. 15 is a perspective view of another embodiment of an alignment device similar to the alignment device of FIGS. 13 and 14.

Referring now to FIG. 15, another embodiment of an alignment device (hereinafter alignment device 412) is shown. The alignment device 412, like the alignment device 352, includes a support arm 192 and a guide arm 194 that are pivotally coupled to a hub 410. The alignment device 412 also includes a user-operated adjustment mechanism 356 that is operable to pivot the arm 194 about an axis 358 and a user-operated adjustment mechanism 370 that is operable to pivot the arm 192 about an axis 372. In contrast to the alignment device 352, position markings 414 are included on the support arm 192 and a guide arm 194 while the pointers 416 are secured to the hub 410.

Figure 16:
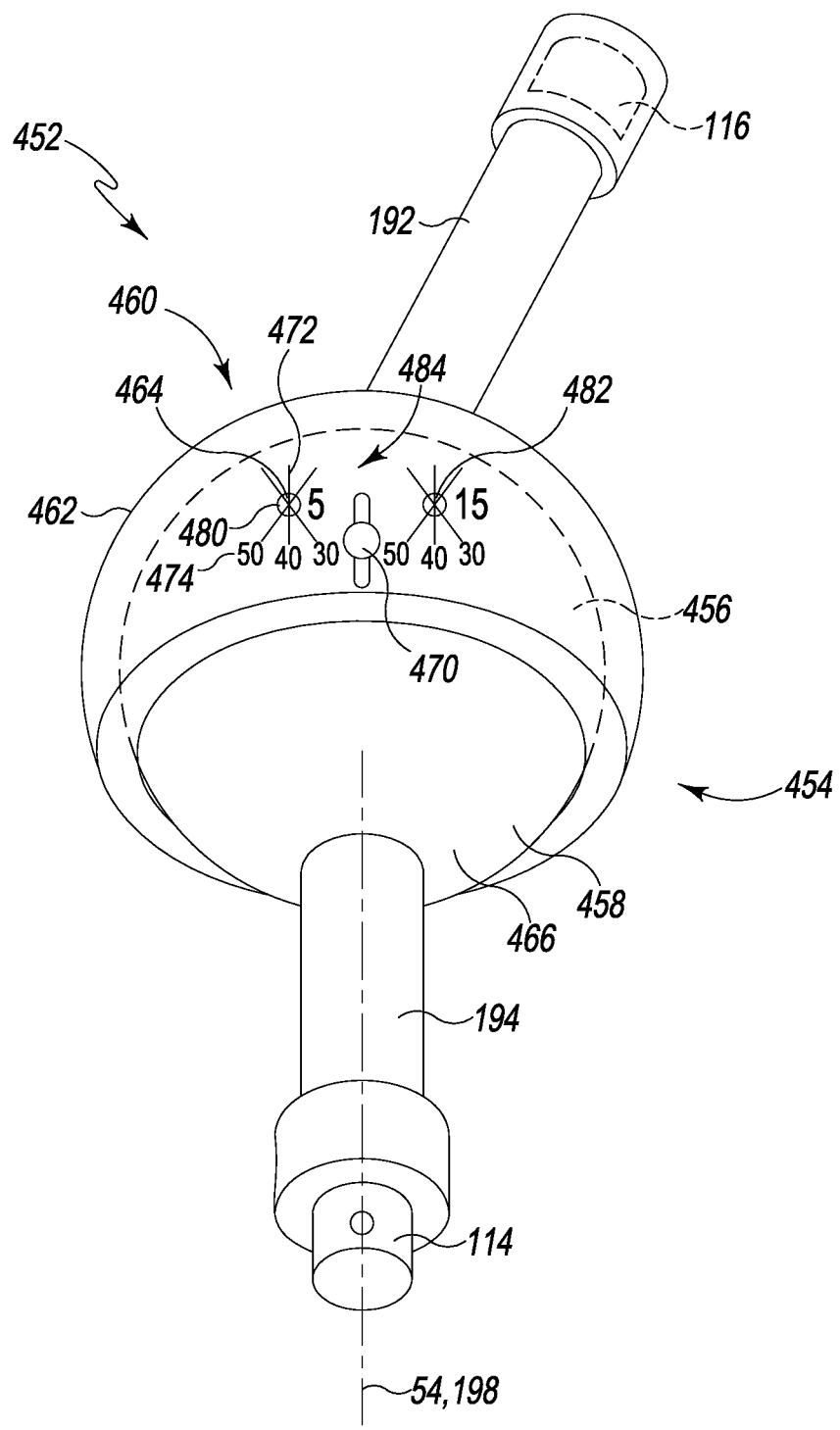
FIG. 16 is a perspective view of another embodiment of an alignment device for the surgical instrument of FIG. 1.

Referring now FIG. 16, another embodiment of an alignment device (hereinafter alignment device 452) is shown. The alignment device 452 permits the surgeon to change the abduction angle and the anteversion angle of the acetabular axis 34 of the prosthetic component 10. Some features of the embodiment illustrated in FIG. 16 are substantially similar to those discussed above in reference to the embodiment of FIGS. 1-12. Such features are designated in FIG. 16 with the same reference numbers as those used in FIGS. 1-12.

The alignment device 452 includes a support arm 192 and a bore 116 defined therein. Similar to the alignment device 52, the dowel pin 114 of the indicator linkage 50 is configured to be received in the bore 116 such that the alignment device 452 may be secured to the indicator linkage 50. The alignment device 452 includes a dowel pin 114 extending from the guide arm 194. As described above, the dowel pin 114 is configured to be received in a bore 116 defined in the upper link 224 of the guide frame 56 such that the alignment device 452 may be secured to the guide frame 56.

The arm 192 is pivotally coupled to the arm 194 via a joint 454. The joint 454 is a spheroid joint that includes a socket 456 defined in the support arm 192. The guide arm 194 includes a ball 458 that is received in the socket 456. The joint 454 permits the guide arm 194 to move about an infinite number of axes relative to the support arm 192, which is fixed in position when the alignment device 452 is secured to indicator linkage 50.

The guide arm 194 of the alignment device 452 has a longitudinal axis 198. The longitudinal axis 198 is coincident with the alignment axis 54 of the alignment device 452. When the guide arm 194 is moved about the joint 454, the orientation of the alignment axis 54 is adjusted to change the magnitudes of the abduction angle α and the anteversion angle β. The alignment device 452 may include a locking device (not shown) that may be operated to lock the guide arm 194 in position relative to the support arm 192 when the surgeon has set the alignment axis 54 at a desired abduction angle α and a desired anteversion angle β.

As shown in FIG. 16, the alignment device 452 includes a position indicator 460 that indicates the magnitudes of the abduction angle α and the anteversion angle β. In the illustrative embodiment, the end 462 of the support arm 192 is semi-transparent such that the ball 458 is visible in the socket 456. The position indicator 460 has a plurality of markings 464 etched into an outer surface 466 of the ball 458. Each of the markings 464 indicates a predetermined position of the acetabular prosthetic component 10 within the patient's surgically-prepared acetabulum 18. The support arm 192 includes a pointer or sight 470 that may be aligned with one of the markings 464.

In the illustrative embodiment, the markings 464 of the position indicator 460 include a plurality of graphical indicators 472 etched or drawn on the surface 466 of the ball 458. The graphical indicators 472 correspond to the plurality of magnitudes of the abduction angle α and the anteversion angle β. The markings 464 also include a plurality of numerical indicators 474 etched or drawn on the surface 466 of the ball 458. The numerical indicators 474 are associated with the graphical indicators 472. As shown in FIG. 16, the graphical indicators 472 include rings 480, 482, and the sight 470 is configured to align with each of the rings 480, 482 based on the orientation of the alignment axis 54. The markings 464 further include side indicators 484, which associate the graphical indicators 472 and the numerical indicators 474 with a particular side of a patient's body (i.e., right or left).

In use, the surgeon may secure the alignment device 452 to the indicator linkage 50 and the guide frame 56 in the manner described above. The surgeon or other user may pivot the guide arm 194 about the joint 454 to change the magnitudes of the abduction angle α and the anteversion angle β of the acetabular prosthetic component 10. When the angle adjustments are complete, the surgeon may insert the acetabular prosthetic component 10 into the patient's surgically-prepared acetabulum 18.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

For example, it should be appreciated that the pelvic reference tool 40 may be utilized to insert a guide shaft into the patient's acetabulum. Such a guide shaft may be used guide a surgical reamer to surgically prepare the patient's acetabulum or guide a trial into position within the acetabulum. In other embodiments, the pelvic reference tool 40 may be utilized directly with the surgical reamer to prepare the patient's acetabulum.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument for positioning an acetabular prosthetic component in a patient's surgically-prepared acetabulum, the instrument comprising:
   a base including a plurality of mounting legs configured to engage the patient's pelvis,
   a first linkage pivotally coupled to the base, the first linkage including a spirit level,
   a locking mechanism operable to lock the first linkage in position relative to the base,
   a second linkage removably coupled to the first linkage, the second linkage having an alignment axis corresponding to a desired abduction angle and a desired anteversion angle of an acetabular axis of the acetabular prosthetic component, and
   a shaft configured to be secured to the acetabular prosthetic component, the shaft having a longitudinal axis that is coincident with the acetabular axis of the acetabular prosthetic component when the acetabular prosthetic component is secured thereto,
   wherein the second linkage includes a parallelogram linkage configured to maintain the acetabular axis of the acetabular prosthetic component parallel with the alignment axis of the second linkage, and the parallelogram linkage includes a mount configured to receive the shaft such that the longitudinal axis extends parallel to the alignment axis.

2. The orthopaedic surgical instrument of claim 1, wherein each mounting leg includes a telescopic shaft and a mounting foot configured to engage the patient's pelvis.

3. The orthopaedic surgical instrument of claim 2, wherein the mounting feet include a pair of mounting feet configured to engage the patient's anterior superior iliac spines of the patient's pelvis and a pair of mounting feet configured to engage the pubic tubercles of the patient's pelvis.

4. The orthopaedic surgical instrument of claim 1, wherein the base includes a frame and each mounting leg is pivotally coupled to the frame.

5. The orthopaedic surgical instrument of claim 1, further comprising a plurality of second linkages, each second linkage having an alignment axis different from the alignment axis of every other second linkage.

6. The orthopaedic surgical instrument of claim 1, wherein the second linkage includes:
   a first adjustment mechanism operable to move a first arm of the second linkage such that the alignment axis corresponds to a second abduction angle, and
   a second adjustment mechanism operable to move the first arm such that the alignment axis corresponds to a second anteversion angle.

7. The orthopaedic surgical instrument of claim 1, wherein:
   the base includes a first mount positioned on a medial side of the base and a second mount positioned on a lateral side of the base, the first mount and the second mount being configured to be coupled to the first linkage, and
   the first linkage is pivotally coupled to the first mount.

8. An orthopaedic surgical instrument for positioning an acetabular prosthetic component in a patient's surgically-prepared acetabulum, the instrument comprising:
   a base configured to engage the patient's pelvis,
   a first linkage coupled to the base, the first linkage including a gravity-based indicator,
   a locking mechanism operable to lock the first linkage in position relative to the base,
   a second linkage coupled to the first linkage, the second linkage having an alignment axis corresponding to a desired abduction angle and a desired anteversion angle of an acetabular axis of the acetabular prosthetic component, and
   a shaft configured to be secured to the acetabular prosthetic component, the shaft having a longitudinal axis that is coincident with the acetabular axis of the acetabular prosthetic component when the acetabular prosthetic component is secured thereto,
   wherein the second linkage includes a parallelogram linkage configured to maintain the acetabular axis of the acetabular prosthetic component parallel with the alignment axis of the second linkage, and the parallelogram linkage includes a mount configured to receive the shaft such that the longitudinal axis extends parallel to the alignment axis.

\* \* \* \* \*